United States Patent [19]

Leland et al.

[11] Patent Number: 5,705,402
[45] Date of Patent: Jan. 6, 1998

[54] METHOD AND APPARATUS FOR MAGNETIC MICROPARTICULATE BASED LUMINESCENCE ASSAY INCLUDING PLURALITY OF MAGNETS

[75] Inventors: Jonathan K. Leland, Laurel; Haresh P. Shah; John H. Kenten, both of Gaithersburg, all of Md.; Jack E. Goodman, Arlington, Va.; George E. Lowke, Laytonsville, Md.; Yuzaburo Namba, Ibaraki, Japan; Gary F. Blackburn, Gaithersburg, Md.; Richard J. Massey, Rockville, Md.

[73] Assignees: Igen International, Inc., Gaithersburg, Md.; Eisai Co. Ltd., Tokyo, Japan

[21] Appl. No.: 255,824

[22] Filed: Jun. 8, 1994

Related U.S. Application Data

[63] Continuation of Ser. No. 827,269, Feb. 3, 1992, abandoned, which is a continuation-in-part of Ser. No. 652,427, Feb. 6, 1991, abandoned, which is a continuation-in-part of Ser. No. 266,882, Nov. 3, 1988, abandoned, and Ser. No. 539,389, Jun. 18, 1990, abandoned, which is a continuation of Ser. No. 266,882, Nov. 3, 1988, abandoned.

[51] Int. Cl.$^6$ ............................................... G01N 33/543
[52] U.S. Cl. ........................... 436/526; 436/518; 436/524; 436/536; 436/537
[58] Field of Search ........................... 436/518, 526, 436/536, 537, 172; 435/7.1; 422/52

[56] References Cited

U.S. PATENT DOCUMENTS

| | | | |
|---|---|---|---|
| 3,970,518 | 7/1976 | Giaeur | 435/239 |
| 4,070,246 | 1/1978 | Kennedy et al. | 428/378 |
| 4,115,535 | 9/1978 | Gialuv | 436/526 |
| 4,169,804 | 10/1979 | Yapel | 252/62.53 |
| 4,280,815 | 7/1981 | Oberhardt et al. | 422/68 |
| 4,305,925 | 12/1981 | Kapmeyer et al. | 436/509 |
| 4,419,453 | 12/1983 | Dorman et al. | 436/534 |
| 4,447,546 | 5/1984 | Hirschfeld | 436/522 |
| 4,480,042 | 10/1984 | Craig et al. | 436/533 |
| 4,515,890 | 5/1985 | Manduino et al. | 435/7.4 |
| 4,539,507 | 9/1985 | Van Slyke et al. | 313/504 |
| 4,554,088 | 11/1985 | Whitehead et al. | 252/62.54 |
| 4,628,037 | 12/1986 | Chagnon et al. | 436/526 |
| 4,652,333 | 3/1987 | Carney | 156/626.1 |
| 4,652,533 | 3/1987 | Tolley | 435/5 |
| 4,661,444 | 4/1987 | Conan | 435/2.9 |
| 4,677,067 | 6/1987 | Schwartz et al. | 435/177 |
| 4,695,392 | 9/1987 | Whitehead et al. | 252/62.54 |
| 4,695,393 | 9/1987 | Chagnon et al. | 252/62.54 |
| 4,698,302 | 10/1987 | Whitehead et al. | 435/94 |
| 4,731,337 | 3/1988 | Luntolo et al. | 436/526 |
| 4,745,077 | 5/1988 | Holian et al. | 436/526 |
| 4,777,145 | 10/1988 | Luntola et al. | 436/526 |
| 4,865,997 | 9/1989 | Stoker | 436/541 |
| 4,916,081 | 4/1990 | Kamada et al. | 436/526 |
| 4,945,045 | 7/1990 | Forrest et al. | 425/25 |
| 4,978,610 | 12/1990 | Forrest et al. | 205/777.5 |
| 5,115,534 | 5/1992 | Fournier | 15/179 |
| 5,147,529 | 9/1992 | Lee et al. | 210/695 |

FOREIGN PATENT DOCUMENTS

| | | |
|---|---|---|
| 0030 087 | 6/1981 | European Pat. Off. . |
| 0180384 | 5/1986 | European Pat. Off. . |
| 1500127 | 2/1978 | United Kingdom . |
| 2005019 | 4/1979 | United Kingdom . |
| 2074727 | 11/1981 | United Kingdom . |
| WO 85/00663 | 2/1985 | WIPO . |
| 85/01253 | 3/1985 | WIPO . |
| 8605815 | 10/1986 | WIPO . |
| WO 86/05815 | 10/1986 | WIPO . |
| 87/00987 | 2/1987 | WIPO . |
| 8706706 | 11/1987 | WIPO . |
| 88/03947 | 6/1988 | WIPO . |
| 89/01814 | 3/1989 | WIPO . |
| 89/04373 | 5/1989 | WIPO . |
| 89/04854 | 6/1989 | WIPO . |
| 89/04859 | 6/1989 | WIPO . |
| 89/04915 | 6/1989 | WIPO . |
| 89/04919 | 6/1989 | WIPO . |
| WO 89/04373 | 12/1989 | WIPO . |
| 90/01370 | 2/1990 | WIPO . |
| 9005301 | 5/1990 | WIPO . |

OTHER PUBLICATIONS

Pourfarzaneh et al. Clin. Chem 26/6 730–733 (1980).
Kohen et al. Alternate Immunoassays Chapter 8 pp. 108–109 John Wiley & Sons Ltd. (W.P. Collins Ed.) 1985.
Abruna, J. Electrochem. Soc. 1985, 132, 842.
Beaucage SL, Caruthers MH. Deoxynucleoside phosphoramidites, a new class of key intermediates for deoxypolynucleotide synthesis. *Tetrahedron Lett* 1982; 22:1859–62.
Cardullo RA, Agrawal S, Flores C, Zamecnik DC, Wolf DE. Detection of nucleic acid hybridization by nonradiative fluorescence resonance energy transfer. *Proc. Natl. Acad. Sci.* 1988; 85:8790–4.
Casadei J, Powell MJ, Kenten JH. Expression and secretion of aequorin as a chimeric antibody using a mammalian expression vector. *Proc. Natl. Acad. Sci.* 1990; 87:2047–51.
Coutlee F, Bobo L, Mayur K, Yolken RH, Viscidi RP. Immunodetection of DNA with biotinylated RNA probes: A study of reactivity of a monoclonal antibody to DNA–RNA hybrids. *Anal. Biochem.* 1989; 181:96–105.
"Devices", Japanese Journal of Applied Physics, vol. 18, No. 7, 1979, 1295–1301.
Dulbecco, R., and Freeman, G., (1959) *Virology* B, 398.
Dynal, Dynabeads, M-450, Dynal A.S. Oslo, Norway, Product Literature.

(List continued on next page.)

*Primary Examiner*—Lora M. Green
*Attorney, Agent, or Firm*—Curtis, Morris & Safford, P.C.; Barry Evans, Esq.; David Rubin, Esq.

[57] ABSTRACT

Disclosed and claimed are methods and apparatus for performing a binding assay for an analyte of interest present in a sample based upon measurement of electrochemiluminescence at an electrode. The method uses magnetically responsive particles. The method and apparatus call for a plurality of electromagnets or permanent magnets in north-south orientation for imposing a magnetic field so as to collect the particles.

8 Claims, 5 Drawing Sheets

OTHER PUBLICATIONS

Ege, et al., J. Anal. Chem. 1984, 56, 2413.

Faulkner, L.R. et al., J. Am. Chem. Soc. 94, 691 (1972).

Hamblen, et al., "Characteristics of an Electrically Controlled Fluorescent Dye Panel", IEEE Conference Record of 1972, Conference on Display Devices, Oct. 11–12, (1972).

Hemingway, et al., "Electrogenerated Chemiluminescence. XXI. Energy Transfer from an Exciplex to a Rare Earth Chelate", J. Am. Chem. Soc. 1975, 97: 1, 200–01.

Heney, G. and Orr, G.A. (1981) Anal. Biochem. 114, 92–96.

Iscove, N.N. and Melchers, F., J. Experimental Medicine 147, 923.

Itaya, et al., "Electrogenerated Chemiluminescence with Solvated Electrons in Hexamethylphosphoramide . 2", J. Am. Chem. Soc. 1978, 100: 19, 5996–6002.

Keszthelyi, et al., "Electrogenerated Chemiluminescence. XV. On the Formation of Excimers and Exciplexes in ECL", Chemical Physics Letters 1974, vol. 24, No. 2, 300–04.

Keszthelyi, et al., "Electrogenerated Chemiluminescence. XIV. Effect of Supporting Electrolyte Concentration and Magnetic Field Effects in the 9, 10–Dimethylanthracene–tri–p–tolylamine in Tetrahydrofuran", Chemical Physics Letters 1973, vol. 23, No. 2, 219, 220–22.

Kohen et al., "Chemiluminescence & Bioluminescence Immunoassay", Alternative Immunoassays, W.P. Collins, (1985) John Wiley & Sons, Ltd., Chap. 8, pp. 103–109.

Ludvik, et al., J. Electroanal. Chem. 1986, 215, 179.

Lyons J, Janssen JWG, Bartram C, Layton M, Mufti GJ. Mutation of Ki–ras and N–ras oncogenes in myelodysplastic syndromes. Blood 1988; 71:1707–12.

Lytle, et al., Photochem. Photobiol. 1971, 13, 123.

Maloy, et al., "Electrogenerated Chemiluminescence. II. The Rotating–Ring Disk Electrode and the Pyrene–N,N,N', N'–Tetramethyl–p–phenylenediamine System", J. Phys. Am. Chem. 1968, vol. 72, No. 12, 4348–50.

Marmur, J. (1961) J. Mol. Biol. 3, 208.

Molecular cloning, a laboratory manual 2nd Ed. Sambrook, J. Cold Spring Harbor Laboratory New York.

Mullis KB, Faloona FA. Specific synthesis of DNA in vitro via a polymerase–catalyzed chain reaction. Methods Enzymol 1987; 155:355–50.

Ngo TT. Procedure for activating polymers with primary and/or secondary hydroxyl group. Makromol Chem. Macromol Symp. 1988; 17:224–39.

Noffsigner, et al., Anal. Chem. 1987, 59, 865.

Pragst, et al., "Electrogenerated Chemiluminescence in Mechanistic Investigations of Electroorganic Reactions, Part I. Cathodic Cleavage of Bis–(2,4,5–Triphenylimidazolyl)–1,2 (Dilophyl)," J. Electroanal. Chem. 1980, 112, 339.

Pragst, et al., J. Electroanal. Chem. 1986, 197, 245.

Reddy EP, Reynolds RK, Santo E, Barbacid M. A point mutation is responsible for the acquisition of the transforming properties by the T24 humanbladder carcinoma oncogene. Nature 1982; 300:149–52.

Rozhitskii, et al., "Steady–State Electrochemiluminescence in Solutions with Organometallic Electrtolytes", J. Appl. Spectrosc. 1978; vol. 28, No. 2, 197–202.

Rubenstein, et al., "Electrogenerated Chemiluminescence Determination of Oxylate", Anal. Chem. 1983, 54, 9, 1580–82.

Rubinstein, et al., J. Am. Chem. Soc. 1981, 103, 512.

Saiki RK, Gelfand DH, Stoffel S, Scharf SJ, Higuchi R, Horn GT, Mullis KB, Erlich HA. Primer–directed enzymatic amplification of DNA with a thermostable DNA polymerase. Science 1988; 239:487–91.

Sato, et al., "Quenching Of Fluorescence in Europium B–Diketone Chelate Solutions and Its Application to Display".

Shibata DK, Arnheim N, Martin JW. Detection of human papilloma virus in paraffin–embedded tissue using the polymerase chain reaction. J. Exp. Med. 1988; 167:225–30.

Smith, J.D., Freeman, G., Vogt, M., and Dulbecco, R., (1960), Virology 12, 155.

Tachikawa, et al., "Electrogenerated Chemiluminescence. Effect on a Magnetic Field on the Delayed Fluorescence and ECL of Several Systems Involving Excimers or Exciplexes", Chemical Physics Letters 1974, vol. 26, No. 4, 568–73.

Tachikawa, et al., "Electrogenerated Chemiluminescence XII. Magnetic Field Effects on ECL in the Tetracene–TMPD System; Evidence for Triplet–Triplet Annihilation of Tetracene", Chemical Physics Letters 1973, vol. 19, No. 2, 287–89.

Tissue Culture Standards Committee, In Vitro 5:2, 93.

Tokel–Takvoryan, et al., "Electrogenerated Chemiluminescence. XIII. Electrochemical and Electrogenerated Chemiluminescence Studies of Ruthenium Chelates", J. Am. Chem. Soc. 1973, 95: 20, 6582–89.

Updyke TV, Nicolson GL. Immunoaffinity isolation of membrane antigens with biotinylated monoclonal antibodies and streptavidin–agarose. Methods Enzymol 1986; 121:717–25.

Weetall, H.H. and Hotaling, T., Biosensors 3 (1987/88), 57–63.

Wheeler, et al., "A Silicon Phthalocyanine and a Silicon Naphthalocyanine: Synthesis, Electrochemistry, and Electrogenerated Chemiluminescence", J. Am. Chem. Soc. 1984, 106, 7404–10.

Wilson, et al., "Electrogenerated Chemiluminescence of trans–Stilbene Derivatives", J. Electrochem. Soc.: Electrochemical Science and Technology (1981), vol. 128, No. 10, 2085–89.

Yanofsky, C. et al. (1981) Nucleic Acids Res. 24, 6647–6668.

Yee C, Krishnan–Hewlett I, Baker CC, Schlegel R, Howly PM. Presence and Expression of Human Papillomavirus sequences in human cervical carcinoma cell lines. Am. J. Pathol. 1985; 199:361–6.

Ziebig, et al., "Intramolecular Exciplexes in the Electrogenerated Chemiluminescence of 1–Amino–3–Anthryl–(9)–Propanes", Journal of Luminescence 21 (1980), 353–66.

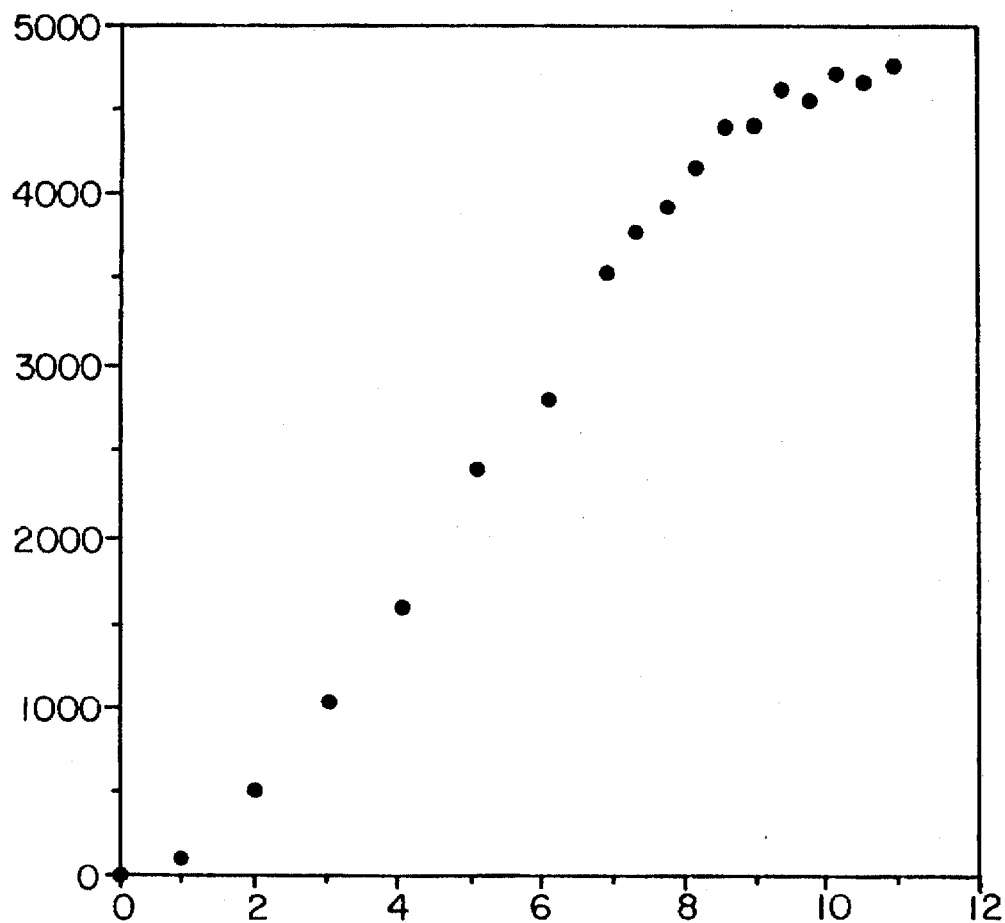
FIG. 6
FIG. 7
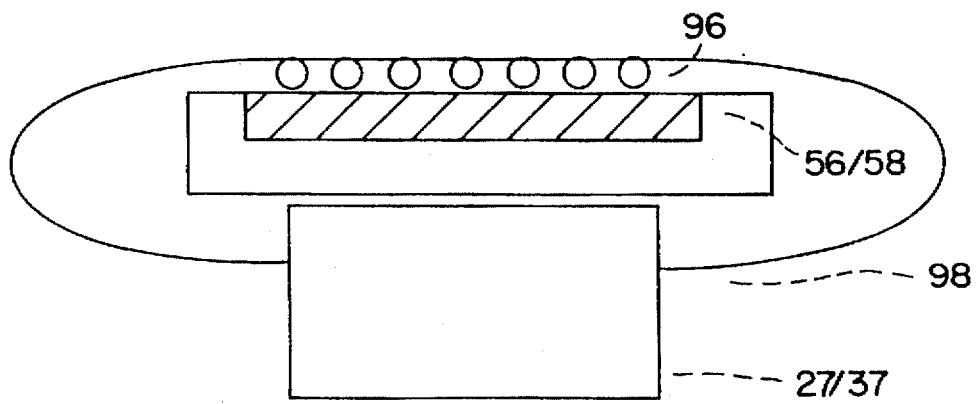

METHOD AND APPARATUS FOR MAGNETIC MICROPARTICULATE BASED LUMINESCENCE ASSAY INCLUDING PLURALITY OF MAGNETS

CROSS REFERENCE TO RELATED APPLICATIONS

This application is a continuation of application Ser. No. 07/827,269, filed Feb. 3, 1992, now abandoned which is a continuation-in-part of application Ser. No. 07/652,427 filed Feb. 6, 1991, now abandoned, which is a continuation-in-part of application Ser. No. 07/266,882 filed Nov. 3, 1988, now abandoned, and also a continuation-in-part of Ser. No. 07/539,389 filed Jun. 18, 1990, now abandoned, which is a continuation of Ser. No. 07/266,882 filed Nov. 3, 1988, now abandoned. All of the above-referenced applications are hereby incorporated herein by reference.

FIELD OF THE INVENTION

This invention relates to a method for performing a binding assay for an analyte of interest present in a sample based upon measurement of electrochemiluminescence at an electrode wherein a complex including the sample, an assay-performance substance containing a component linked to a label capable of being induced to electrochemiluminesce, and a plurality of magnetically responsive suspended particles capable of binding with the analyte or substance is formed; the complex is collected at the surface of an electrode by the imposition of a magnetic field on the particles by a plurality of permanent magnets or electromagnets in north-south orientation; the label is induced to luminesce; and, the luminescence emitted is measured. The invention also relates to apparatus for performing such a method having the plurality of permanent magnets or electromagnets in north-south orientation.

BACKGROUND OF THE INVENTION

Numerous methods and systems have been developed for the detection and quantitation of analytes of interest in biochemical and biological substances. Methods and systems which are capable of measuring trace amounts of microorganisms, pharmaceuticals, hormones, viruses, antibodies, nucleic acids and other proteins are of great value to researchers and clinicians.

A very substantial body of art has been developed based upon the well known binding reactions, e.g., antigen-antibody reactions, nucleic acid hybridization techniques, and protein-ligand systems. The high degree of specificity in many biochemical and biological binding systems has led to many assay methods and systems of value in research and diagnostics. Typically, the existence of an analyte of interest is indicated by the presence or absence of an observable "label" attached to one or more of the binding materials. Of particular interest are labels which can be made to luminesce through photochemical, chemical, and electrochemical means. "Photoluminescence" is the process whereby a material is induced to luminesce when it absorbs electromagnetic radiation. Fluorescence and phosphorescence are types of photoluminescence. "Chemiluminescent" processes entail the creation of luminescent species by chemical transfer of energy. "Electrochemiluminescence" entails creation of luminescent species electrochemically.

Chemiluminescent assay techniques where a sample containing an analyte of interest is mixed with a reactant labeled with a chemiluminescent label have been developed. The reactive mixture is incubated and some portion of the labeled reactant binds to the analyte. After incubation, the bound and unbound fractions of the mixture are separated and the concentration of the label in either or both fractions can be determined by chemiluminescent techniques. The level of chemiluminescence determined in one or both fractions indicates the amount of analyte of interest in the biological sample.

Electrochemiluminescent (ECL) assay techniques are an improvement on chemiluminescent techniques. They provide a sensitive and precise measurement of the presence and concentration of an analyte of interest. In such techniques, the incubated sample is exposed to a voltammetric working electrode in order to trigger luminescence. In the proper chemical environment, such electrochemiluminescence is triggered by a voltage impressed on the working electrode at a particular time and in a particular manner. The light produced by the label is measured and indicates the presence or quantity of the analyte. For a fuller description of such ECL techniques, reference is made to PCT published application US85/01253 (WO86/02734), PCT published application number US87/00987, and PCT published application U.S. Ser. No. 88/03947. The disclosures of the aforesaid applications are incorporated by reference.

It is desirable to carry out electrochemiluminescent assays without the need for a separation step during the assay procedure and to maximize the signal modulation at different concentrations of analyte so that precise and sensitive measurements can be made. Among prior art methods for nonseparation assays are those which employ microparticulate matter suspended in the assay sample to bind one or more of the binding components of the assay.

U.S. Pat. No. 4,305,925 relates to the detection and determination of clinically relevant proteins and peptides by means of nephelometric and turbidimetric methods. The methods disclosed involve binding the antigen or antibody to latex particles which perform the function of light scattering or adsorption.

U.S. Pat. No. 4,480,042 relates to techniques employing particle reagents consisting of shell-core particles. The shell contains functional groups to which compounds of biological interest can be covalently bonded, and the high refractive index of the core results in high sensitivity to light scattering measurements. The technique is based upon agglutination reactions which result from the reaction of bivalent antibodies with multivalent antigens of interest to produce aggregates which can be detected and/or measured in various ways.

U.S. Pat. No. 4,419,453 likewise relates to the use of colored latex agglutination test methods useful for detecting the presence of immunochemicals such as antibodies and immunogens.

Based upon this prior art, it would not have appeared possible to use microparticulate matter in assays wherein a luminescent phenomenon is measured. One would expect that the luminescence from free chemiluminescent or electrochemiluminescent moieties would be absorbed, scattered, or otherwise suffer interference from the microparticulate matter.

Contrary to that expectation, U.S. application Ser. No. 539,389 now abandoned (PCT published application U.S. Ser. No. 89/04919) teaches sensitive, specific binding assay methods based on a luminescent phenomenon wherein inert microparticulate matter is specifically bound to one of the binding reactants of the assay system. The assays may be performed in a heterogeneous (one or more separation steps)

assay format and may be used most advantageously in a homogeneous (nonseparation) assay format.

U.S. Ser. No. 89/04919 relates to a composition for an assay based upon a binding reaction for the measurement of luminescent phenomenon, which composition includes a plurality of suspended particles having a surface capable of binding to a component of the assay mixture. In another aspect, it is directed to a system for detecting or quantitating an analyte of interest in a sample, which system is capable of conducting the assay methods using the assay compositions of the inventions. The system includes means for inducing the label compound in the assay medium to luminesce, and means for measuring the luminescence to detect the presence of the analyte of interest in the sample.

It was found that the binding of that component of the assay system to which an electrochemiluminescent moiety has been linked, to suspended microparticulate matter, greatly modulates the intensity of the luminescent signal generated by the electrochemiluminescent moiety linked to that component, thereby providing a means of monitoring the specific binding reaction of the assay system. Even more surprisingly, the suspended particles were found to have little or no effect on the intensity of the luminescent signal generated by the electrochemiluminescent moiety linked to the component of the system which remains unbound to the suspended microparticulate matter.

Thus, U.S. Ser. No. 89/04919 is directed to methods for the detection of an analyte of interest in a sample, which method includes the steps of (1) forming a composition comprising (a) a sample suspected of containing an analyte of interest, (b) an assay-performance-substance selected from the group consisting of (i) analyte of interest or analog of the analyte of interest, (ii) a binding partner of the analyte of interest or its said analog, and (iii) a reactive component capable of binding with (i) or (ii), wherein one of said substances is linked to a label compound having a chemical moiety capable of being induced to luminesce, and (c) a plurality of suspended particles capable of specifically binding with the analyte and/or a substance defined in (b)(i), (ii), or (iii); (2) incubating the composition to form a complex which includes a particle and said label compound; (3) inducing the label compound to luminesce; and (4) measuring the luminescence emitted by the composition to detect the presence of the analyte of interest in the sample. Those same methods may be used to quantify the amount of analyte in a sample by comparing the luminescence of the assay composition to the luminescence of a composition containing a known amount of analyte.

Analogs of the analyte of interest, which may be natural or synthetic, are compounds which have binding properties comparable to the analyte, but include compounds of higher or lower binding capability as well. Binding partners suitable for use in the present invention are well-known. Examples are antibodies, enzymes, nucleic acids, lectins, cofactors and receptors. The reactive components capable of binding with the analyte or its analog and/or with a binding partner thereof may be a second antibody or a protein such as Protein A or Protein G or may be avidin or biotin or another component known in the art to enter into binding reactions.

Advantageously, the luminescence arises from electrochemiluminescence (ECL) induced by exposing the label compound, whether bound or unbound to specific binding partners, to a voltammetric working electrode. The ECL reactive mixture is controllably triggered to emit light by a voltage impressed on the working electrode at a particular time and in a particular manner to generate light. Although the emission of visible light is an advantageous feature the composition or system may emit other types of electromagnetic radiation, such as infrared or ultraviolet light, X-rays, microwaves, etc. Use of the terms "electrochemiluminescence," "electrochemiluminescent," "luminescence," "luminescent," and "luminesce" includes the emission of light and other forms of electromagnetic radiation.

The methods taught in U.S. Ser. No. 89/04919 permit the detection and quantitation of extremely small quantities of analytes in a variety of assays performed in research and clinical settings. The demands of researchers and clinicians makes it imperative, however, to lower the detection limits of assays performed by these methods to increase the sensitivities of those assays and to increase the speed at which they can be performed.

Various methods are known in the art for increasing the signal from labeled species by concentrating them before subjecting them to a measurement step. In U.S. Pat. No. 4,652,333, for example, particles labeled with fluorescent, phosphorescent or atomic fluorescent labels are concentrated by microfiltration before a measurement step is performed.

It is also known in the art to concentrate labeled immunochemical species prior to a measurement step, by, e.g., drawing magnetically responsive labeled particles to the surface of a measurement vessel. In U.S. Pat. Nos. 4,731,337, 4,777,145, and 4,115,535, for example, such particles are drawn to the vessel wall and then are irradiated to excite a fluorophoric emission of light.

In U.S. Pat. No. 4,945,045, particles are concentrated on a magnetic electrode. An electrochemical reaction takes place at the electrode facilitated by a labeled chemical mediator. The immunochemical binding reaction alters the efficiency of the mediator resulting in a modulated signal when binding takes place.

These prior art methods are not relevant to the surface selective excitation processes of the invention. While not being bound by any particular mechanistic explanation of surface excitation, e.g., electrochemiluminescence, it is believed that the label on the solid-phase complex must be oxidized at the electrode. This requires that an electron move from the label to the electrode. It is believed that the electron makes this "jump" by a phenomenon known as tunneling in which the electron passes through space (a region where its potential energy is very high, e.g., the solution) without having to go "over" the potential energy barrier. It can tunnel through the energy barrier, and thus, move from one molecule to another or from one molecule to an electrode without additional energy input. However, this tunneling phenomenon can only operate for very short distances. The probability of the tunneling phenomenon falls off exponentially as the distance between the two species increases. The probability of the tunneling phenomenon occurring between two species is fairly high if the distance is less than 25 Angstroms (2.5 nm) but is fairly low if the distance is greater. The distance of 25 Å is a rule-of-thumb used by those skilled in the art but is not an absolute limitation.

Accordingly, only those ECL labels with 25 Å of the surface of the electrode can be expected to participate in the ECL process. The area of the particle which is within 25 Å of the surface of an electrode is typically extremely small.

Accordingly, one would not expect that ECL from a particle surface would be measurable to any significant degree. Moreover, the light which is produced by the ECL process must pass through the particle to get to the photomultiplier. Since the particles are essentially opaque (a concentrated suspension of them is black) one would not expect that, even if significant amounts of light could be produced by ECL, that the light could pass through the particle and be measured by the photomultiplier. Moreover, the art does not teach or suggest the plurality of north-south magnets which is particular to the method and apparatus of this invention.

OBJECTS OF THE INVENTION

It is an object of this invention to provide separation (heterogeneous) or non-separation (homogeneous), specific bonding methods and apparatus, based upon the measurement of electrochemiluminescence emitted from an assay composition containing magnetic microparticulate matter and employing a plurality of north-south oriented magnets.

It is a further and related object to provide such methods and apparatus having improved sensitivity, faster assay time, greater specificity, lower detection limits and greater precision than has heretofore been achieved.

DESCRIPTION OF THE INVENTION

DEFINITION OF TERMS

The term "ECL moiety," "metal-containing ECL moiety" "label," "label compound," and "label substance," are used interchangeably. It is within the scope of the invention for the species termed "ECL moiety," "metal-containing ECL moiety," "organo-metallic," "metal chelate," "transition metal chelate" "rare earth metal chelate," "label compound," "label substance" and "label" to be linked to molecules such as an analyte or an analog thereof, a binding partner of the analyte or an analog thereof, and further binding partners of such aforementioned binding partner, or a reactive component capable of binding with the analyte, an analog thereof or a binding partner as mentioned above. The above-mentioned species can also be linked to a combination of one or more binding partners and/or one or more reactive components. Additionally, the aforementioned species can also be linked to an analyte or its analog bound to a binding partner, a reactive component, or a combination of one or more binding partners and/or one or more reactive components. It is also within the scope of the invention for a plurality of the aforementioned species to be bound directly, or through other molecules as discussed above, to an analyte or its analog. For purposes of brevity, these ligands are referred to as an assay-performance-substance.

The terms detection and quantitation are referred to as "measurement", it being understood that quantitation may require preparation of reference compositions and calibrations.

The terms collection and concentration of complex may be used interchangeably to describe the concentration of complex within the assay composition and the collection of complex at, e.g., an electrode surface.

BRIEF DESCRIPTION OF THE DRAWINGS

FIG. 6 is a graph showing the increase in ECL intensity as a function of time in assays conducted with the cell of FIG. 5, i.e., the effect of collection time on ECL intensity.

FIG. 7 is a schematic representation of the lines of force in the vicinity of the electrode surface of the magnets (FIGS. 1 and 2) beneath the electrode surface.

BRIEF DESCRIPTION OF THE INVENTION

Figure 1:
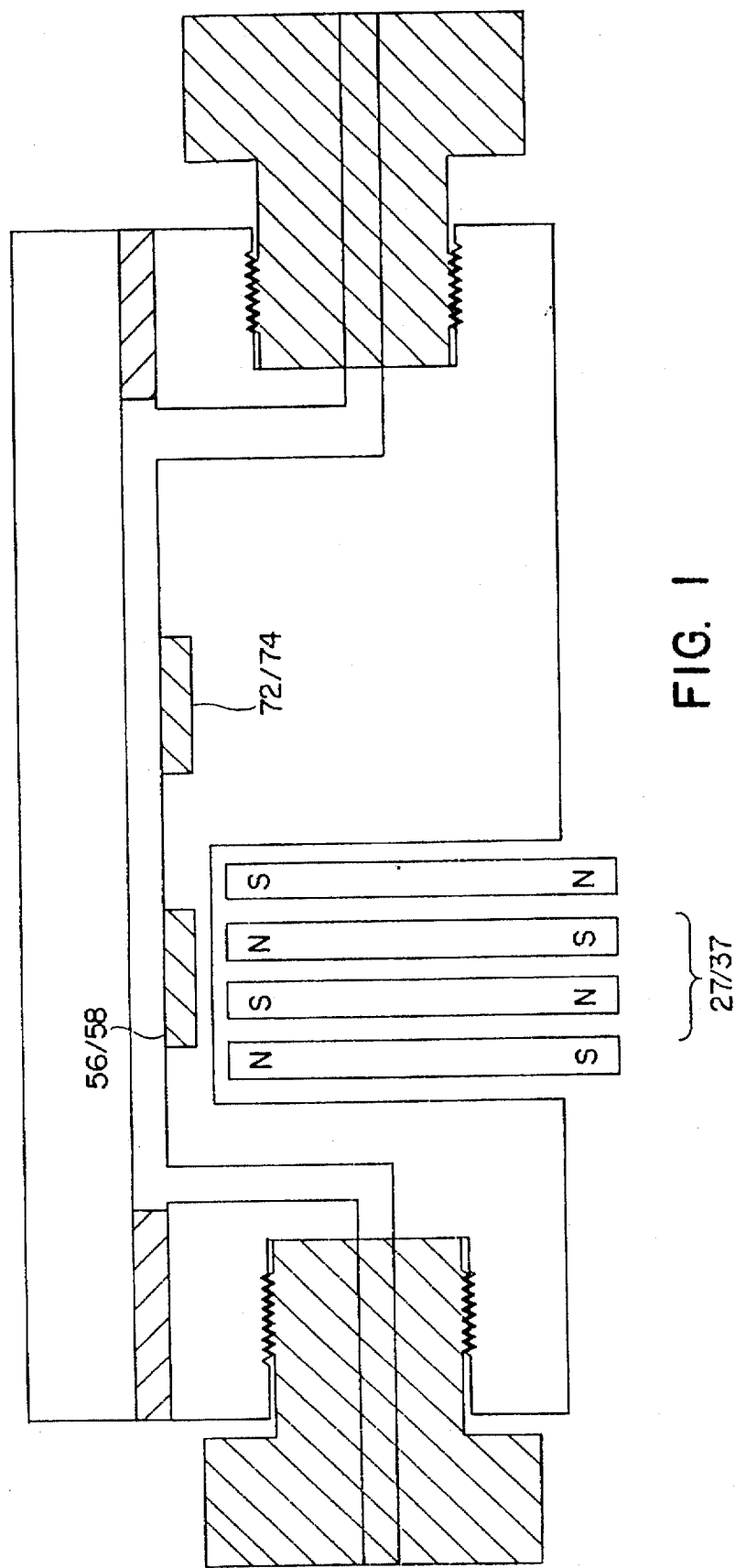
FIGS. 1 and 2 show the cell and plurality of magnets for performing the magnetic microparticulate-based separation or non-separation assay method of the invention; the plurality of magnets of the magnet system imposes field lines which are largely parallel to the plane of the electrode surface.

In its broadest embodiment, the invention is in a method for performing a binding assay for an analyte of interest present in a sample. The steps include:

(a) forming a composition containing
  (i) said sample
  (ii) an assay-performance-substance which contains a component linked to a label compound capable of being induced to electrochemiluminesce, and
  (iii) a plurality of magnetically responsive suspended particles capable of specific binding with the analyte and or said assay-performance-substance;

(b) incubating said composition to form a complex which includes a particle and said label compound;

(c) introducing said composition into an assay cell;

(d) collecting said complex at the surface of an electrode by imposition of a magnetic field on said particles;

(e) inducing the label compound in said collected complex to luminescence by imposing a voltage on said electrode; and (f) measuring the emitted luminescence at the electrode surface to measure the presence of the analyte of interest in the sample; wherein a plurality of magnets, permanent magnets or electromagnets, in north-south orientation are positioned vertically below a horizontally oriented electrode surface.

The invention also provides an apparatus for performing a binding assay for an analyte of interest present in a sample based upon measurement of electrochemiluminescence at an electrode surface comprising:

(a) a cell defining an assay sample containing volume and having inlet and outlet means, an electrode, and further including means for obtaining a substantially even distribution of said complex on said electrode surface;

(b) means to impress a voltage upon said electrode; and (c) means to measure the electrochemiluminescence generated at said electrode; the means for obtaining an even distribution of complex includes means for generating a magnetic field oriented with respect to said electrode so that the lines of force of said magnetic field are substantially parallel with the surface of said electrode in the region of said surface; and the means for generating a magnetic field includes a plurality of magnets in north-south orientation and separated by non-magnetic material positioned vertically below said electrode.

Several different heterogeneous and homogeneous formats for binding assays can be implemented using the method described above to collect and concentrate the complex on the surface of an electrode. In a heterogeneous binding assay the complex is separated from the composition before measuring luminescence from the label. In homogeneous assays, no separation of the bound (to the solid phase) and unbound labeled reagents is made.

In a heterogeneous assay, when the complex is concentrated on the surface of the working electrode, the measured signal from the label is much greater than it would be in the absence of a collection step. The signal from the uncomplexed labeled reagents, in contrast, is not changed. Hence, despite the presence of the uncomplexed labeled reagents in the measurement cell, the signal from the collected complex is stronger than in an assay without collection of complex. The detection limit for the binding assay is, much improved as a result of the collection procedure.

In the invention, an in-situ separation step can be included in the homogeneous binding assay procedure. After the assay composition, i.e., sample, assay performance substance and particles have been pumped into the measurement cell and the complex captured upon the working electrode, a second fluid is pumped through the cell which is free of label or labeled reagents, thereby performing an in-situ wash or separation of the complex from unbound components of the assay composition. This assay procedure is technically a heterogeneous binding assay. However, the ability to perform the separation inside the measurement cell is advantageous in that it does not require additional separation apparatus and the procedure is generally much faster than external separation methods.

Heterogeneous binding assays are conducted using the invention by mixing the components of the assay composition and allowing them to react for a predetermined length of time. The assay composition is then subjected to a separation step wherein the solution is separated from the particles. Electrochemiluminescence is then measured from either the complex or the solution. Measuring the ECL from the complex after a concentration step permits measurement of analyte with better accuracy and with a lower detection limit than is possible without concentration.

DETAILED DESCRIPTION OF THE INVENTION

The invention, as well as other objects and features thereof, will be understood more clearly and fully from the following description of certain preferred embodiments.

The invention is broadly applicable to analytes of interest which are capable of entering into binding reactions. These reactions include, e.g., antigen-antibody, ligand receptor, DNA and RNA interactions, and other known reactions. The invention relates to a method and apparatus for qualitatively and quantitatively detecting the presence of such analytes of interest in a multicomponent sample; the method and apparatus involve a plurality of north-south magnets.

The Samples

The sample which may contain the analyte of interest, which may be in solid, emulsion, suspension, liquid, or gas form, may be derived from, for example, cells and cell-derived products, water, food, blood, serum, hair, sweat, urine, feces, tissue, saliva, oils, organic solvents or air. The sample may further comprise, for example, water, acetonitrile, dimethyl sulfoxide, dimethyl formamide, n-methyl-pyrrolidone or alcohols or mixtures thereof.

The Analytes

Typical analytes of interest are a whole cell or surface antigen, subcellular particle, virus, prion, viroid, antibody, antigen, hapten, fatty acid, nucleic acid, protein, lipoprotein, polysaccharide, lipopolysaccharide, glycoprotein, peptide, polypeptide, cellular metabolite, hormone, pharmacological agent, synthetic organic molecule, organometallic molecule, tranquilizer, barbiturate, alkaloid, steroid, vitamin, amino acid, sugar, lectin, recombinant or derived protein, biotin, avidin, streptavidin, or inorganic molecule present in the sample. Typically, the analyte of interest is present at a concentration of $10^{-3}$ molar or less, for example, as low as $10^{-12}$ molar or lower.

Assay-Performance-Substance

The assay-performance-substance which is combined with the sample containing the analyte of interest contains at least one substance selected from the group consisting of (i) added analyte of interest or its analog, as defined above, (ii) a binding partner of the analyte of interest or its said analog, and (iii) a reactive component, as defined above, capable of binding with (i) or (ii), wherein one of said substances is linked to a compound or moiety, e.g. an ECL moiety capable of being induced to luminesce. The labeled substance may be a whole cell or surface antigen, a subcellular particle, virus, prion, viroid, antibody, antigen, hapten, lipid, fatty acid, nucleic acid, polysaccharide, protein, lipoprotein, lipopolysaccharide, glycoprotein, peptide, polypeptide, cellular metabolite, hormone, pharmacological agent, tranquilizer, barbiturate, alkaloid, steroid, vitamin, amino acid, sugar, nonbiological polymer (preferably soluble), lectin, recombinant or derived protein, synthetic organic molecule, organometallic molecule, inorganic molecule, biotin, avidin or streptavidin. In one embodiment, the reagent is an electrochemiluminescent moiety conjugated to an antibody, antigen, nucleic acid, hapten, small nucleotide sequence, oligomer, ligand, enzyme, or biotin, avidin, streptavidin, Protein A, Protein G, or complexes thereof, or other secondary binding partner capable of binding to a primary binding partner through protein interactions.

Analogs of the analyte of interest, which can be natural or synthetic, are typically compounds which have binding properties comparable to the analyte, but can also be compounds of higher or lower binding capability. The reactive component capable of binding with the analyte or its analog, and/or with a binding partner thereof, and through which the ECL moiety can be linked to the analyte, is suitably a second antibody or a protein such as Protein A or Protein G, or avidin or biotin or another component known in the art to enter into binding reactions.

The Labels

Advantageously, the ECL moieties are metal chelates. The metal of that chelate is suitably any metal such that the metal chelate will luminesce under the electrochemical conditions which are imposed on the reaction system in question. The metal of such metal chelates is, for instance, a transition metal (such as a d-block transition metal) or a rare earth metal. The metal is preferably ruthenium, osmium, rhenium, iridium, rhodium, platinum, indium, palladium, molybdenum, technetium, copper, chromium or tungsten. Especially preferred are ruthenium and osmium.

The ligands which are linked to the metal in such chelates are usually heterocyclic or organic in nature, and play a role in determining whether or not the metal chelate is soluble in an aqueous environment or in an organic or other nonaqueous environment. The ligands can be polydentate, and can be substituted. Polydentate ligands include aromatic and aliphatic ligands. Suitable aromatic polydentate ligands include aromatic heterocyclic ligands. Preferred aromatic heterocyclic ligands are nitrogen-containing, such as, for example, bipyridyl, bipyrazyl, terpyridyl, and phenanthrolyl. Suitable substituents include for example, alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxysuccinimide. The chelate may have one or more monodentate ligands, a wide variety of which are known to the art. Suitable monodentate ligands include, for example, carbon monoxide, cyanides, isocyanides, halides, and aliphatic, aromatic and heterocyclic phosphines, amines, stilbenes, and arsines.

Examples of suitable chelates are bis [(4,4'-carbomethoxy)-2,2'-bipyridine]2-[3-(4-methyl-2,2'-bipyridine-4-yl)propyl]-1,3-dioxolane ruthenium (II); bis(2, 2'bipyridine) [4-(butan-1-al)-4'-methyl-2,2'-bipyridine] ruthenium (II); bis(2,2'-bipyridine) [4-(4'-methyl-2,2'-bipyridine-4'-yl)-butyric acid]ruthenium (II); tris(2, 2'bipyridine)ruthenium (II); (2,2'bipyridine) [bis-bis(1,2-diphenylphosphino)ethylene]2-[3-(4-methyl-2,2'-bipyridine-4'-yl)propyl]-1,3-dioxolane osmium (II); bis(2, 2'-bipyridine) [4-(4'-methyl-2,2'-bipyridine)-butylamine] ruthenium (II); bis(2,2'-bipyridine) [1-bromo-4(4'-methyl-2, 2'-bipyridine-4-yl)butane]ruthenium (II); bis(2,2'bipyridine) maleimidohexanoic acid, 4-methyl-2,2'-bipyridine-4'-butylamide ruthenium (II). Other ECL moieties are described in PCT published application US87/00987 and PCT published application 88/0394, incorporated herein by reference.

The function of the ECL moieties is to emit electromagnetic radiation as a result of introduction into the reaction system of electrochemical energy. In order to do this, they must be capable of being stimulated to an excited energy state and also capable of emitting electromagnetic radiation, such as a photon of light, upon descending from that excited state. While not wishing to be bound by theoretical analysis of the mechanism of the ECL moiety's participation in the electrochemiluminescent reaction, we believe that it is oxidized by the introduction of electrochemical energy into the reaction system and then, through interaction with a reductant present in the system, is converted to the excited state. This state is relatively unstable, and the metal chelate quickly descends to a more stable state. In so doing, the chelate gives off electromagnetic radiation, such as a photon of light, which is detectable.

The amount of metal chelate or other metal-containing ECL moiety incorporated in accordance with the invention will vary from system to system. Generally, the amount of such moiety utilized is that amount which is effective to result in the emission of a detectable, and if desired, quantitatable, emission of electromagnetic energy, from the aforementioned composition or system. The detection and/or quantitation of an analyte of interest is typically made from a comparison of the luminescence from a sample containing an analyte of interest and an ECL moiety to the luminescence emitted by a calibration standard developed with known amounts of the analyte of interest and ECL moiety. This assumes a homogeneous format. In the heterogeneous mode, a separation as discussed previously is carried out prior to ECL analysis.

As can be appreciated by one of ordinary skill in the art, the identity and amount of the metal-containing ECL moiety will vary from one system to another, depending upon prevailing conditions. The appropriate metal-containing ECL moiety, and sufficient amount thereof to obtain the desired result, can be determined empirically by those of ordinary skill in the art, once equipped with the teachings herein, without undue experimentation.

The Particles

The particles advantageously comprise micro-particulate matter having a diameter of 0.001 to 200 µm, such as 0.05 µm to 200 µm, preferably 0.1 µm to 100 µm, most preferably 0.5 µm to 10 µm, and a surface component capable of binding to the analyte and/or one or more of the other substances defined above. For example, the microparticulate matter may be crosslinked starch, dextrans, cellulose, proteins, organic polymers, styrene copolymer such as styrene/butadiene copolymer, acrylonitrile/butadiene/styrene copolymer, vinylacetyl acrylate copolymer, or vinyl chloride/acrylate copolymer, inert inorganic particles, chromium dioxide, oxides of iron, silica, silica mixtures, and proteinaceous matter, or mixtures thereof. Desirably, the particles are suspended in the ECL system. However, the particles must be or must include magnetically responsive particles. It is also noted that samples, analytes, assay-performance-substances, labels, assay media, reagents and other assay components, and particles, including any of the aforementioned in combination, as well as any components of the aforementioned, are not per se contemplated as within the scope of the invention.

Assay Media

In order to operate a system in which an electrode introduces electrochemical energy, it is necessary to provide an electrolyte in which the electrode is immersed and which contains the ECL moiety. The electrolyte is a phase through which charge is carried by ions. Generally, the electrolyte is in the liquid phase, and is a solution of one or more salts or other species in water, an organic liquid or mixture of organic liquids, or a mixture of water and one or more organic liquids. However, other forms of electrolyte are also useful in certain embodiments of the invention. For example, the electrolyte may be a dispersion of one or more substances in a fluid—e.g., a liquid, a vapor, or a supercritical fluid—or may be a solution of one or more substances in a solid, a vapor or supercritical fluid.

The electrolyte is suitably a solution of a salt in water. The salt can be a sodium salt or a potassium salt preferably, but incorporation of other cations is also suitable in certain embodiments, as long as the cation does not interfere with the electrochemiluminescent interaction sequence. The salt's anion may be a phosphate, for example, but the use of other anions is also permissible in certain embodiments of the invention—once again, as long as the selected anion does not interfere with the electrochemiluminescent interaction sequence.

The composition may also be nonaqueous. While supercritical fluids can in certain instances be employed advantageously, it is more typical to utilize an electrolyte comprising an organic liquid in a nonaqueous composition. Like an aqueous electrolyte, the nonaqueous electrolyte is also a phase through which charge is carried by ions. Normally, this means that a salt is dissolved in the organic liquid medium. Examples of suitable organic liquids are acetonitrile, dimethylsulfoxide (DMSO), dimethylformamide (DMF), methanol, ethanol, and mixtures of two or more of the foregoing. Illustratively, tetraalkylammonium salts, such as tetrabutylammonium tetrafluoroborate, which are soluble in organic liquids can be used with them to form nonaqueous electrolytes.

The electrolyte is, in certain embodiments of the invention, a buffered system. Phosphate buffers are often advantageous. Examples are an aqueous solution of sodium phosphate/sodium chloride, and an aqueous solution of sodium phosphate/sodium fluoride.

Other Assay Components

As described PCT published application U.S. Ser. No. 89/04859, entitled Electrochemiluminescent Reaction Utilizing Amine-Derived Reductant, the disclosure of which is incorporated by reference, it is desirable to include a reductant, typically an amine or amine moiety (of a larger molecule) which can be oxidized and spontaneously decomposed to convert it into a highly reducing species. It is believed that the amine or amine moiety is also oxidized by electrochemical energy introduced into the reaction system. The amine or amine moiety loses one electron, and then deprotonates, or rearranges itself, into a strong reducing agent. This agent interacts with the oxidized metal-containing ECL moiety and causes it to assume the excited state discussed above. In order to carry out its role, the amine or amine moiety preferably has a carbon-centered radical with an electron which can be donated from such carbon, and an alpha carbon which can then act as a proton donor during deprotonation in order to form the reductant. The amine-derived reductant provides the necessary stimulus for converting the metal-containing ECL moiety to its excited state, from which detectable electromagnetic radiation is emitted.

A wide range of amines and corresponding amine moieties can be utilized in practicing the present invention. Generally, the amine or amine moiety is chosen to suit the pH of the system which is to be electrochemiluminescently analyzed. Another relevant factor is that the amine or amine moiety should be compatible with the environment in which it must function during analysis, i.e., compatible with an aqueous or nonaqueous environment, as the case may be. Yet another consideration is that the amine or amine moiety selected should form an amine-derived reductant under prevailing conditions which is strong enough to reduce the oxidized metal-containing ECL moiety in the system.

Amines (and corresponding moieties derived therefrom) which are advantageously utilized in the present invention are aliphatic amines, such as primary, secondary and tertiary alkyl amines, the alkyl groups of each having from one to three carbon atoms, as well as substituted aliphatic amines. Tripropyl amine is an especially preferred amine as it leads to, comparatively speaking, a particularly high-intensity emission of electromagnetic radiation, which enhances the sensitivity and accuracy of detection and quantitation with embodiments in which it is used. Also suitable are diamines, such as hydrazine, and polymines, such as poly(ethyleneimine). Examples of other amines suitable for practicing the invention are triethanol amine, triethyl amine, 1,4-diazabicyclo-(2.2.2)-octane, 1-piperidine ethanol, 1,4-piperazine-bis-(ethane-sulfonic acid), tri-isopropyl amine and poly(ethyleneimine).

Typically, the metal-containing ECL moiety utilized in the present invention is the reaction-limiting constituent. Accordingly, it is also typical that the amine or amine moiety is provided in a stoichiometric excess with respect thereto. Illustratively, the amine or amine moiety is employed in a concentration of 50–150 mM. For utilization at a pH of approximately 7, a concentration of 100 mM is often advantageous. In certain embodiments, the upper limit on amine or amine moiety concentration is determined by the maximum solubility of the amine or moiety in the environment in which it is being used, for example in water. In general, the amount of amine or amine moiety employed is that which is sufficient to effect the transformation of the oxidized metal-containing ECL moiety into its excited state so that luminescence occurs. Those of ordinary skill in the art, equipped with the teachings herein, can determine empirically the amount of amine or amine moiety advantageously used for the particular system being analyzed, without undue experimentation.

As described in PCT published application U.S. Ser. No. 89/04915, entitled Enhanced Electrochemiluminescent Reaction, the contents of which are incorporated by reference, the assays of the invention are desirably carried out in the presence of an enhancer, typically a compound of the formula

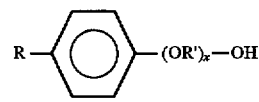

wherein R is hydrogen or $C_nH_{2n+1}$, R' is $C_nH_{2n}$, X is 0 to 70, and n is from 1 to 20. Preferably, n can be from 1 to 4. Specific examples are a substance available in commerce under the name Triton X-100, of the formula

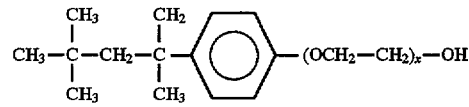

wherein x is 9–10, and a substance available in commerce under the name Triton N-401 (NPE-40), of the formula

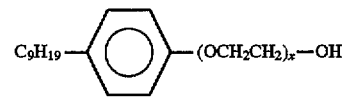

wherein x is 40. The enhancer is generally utilized in an amount sufficient so that in its presence the desired increase in emission of electromagnetic radiation occurs. Typically, the amount is 0.01% to 5.0%, more specifically 0.1% to 1.0%, v/v.

The ECL moiety used in the present invention is induced to emit electromagnetic radiation by stimulating it into an excited state. This is accomplished by exposing the system in which the ECL moiety is incorporated to electrochemical energy. The potential at which oxidation of the ECL moiety and the species forming a strong reductant occurs depends upon the exact chemical structures thereof, as well as factors such as the pH of the system and the nature of the electrode used to introduce electrochemical energy. It is well known to those of ordinary skill in the art how to determine the optimal potential and emission wavelength of an electrochemiluminescent system. Certain preferred methods of stimulating the ECL system are disclosed in PCT published application U.S. Ser. No. 89/01814, the contents of which are incorporated herein by reference.

Apparatus for Measuring Electrochemiluminescence

Figure 8:
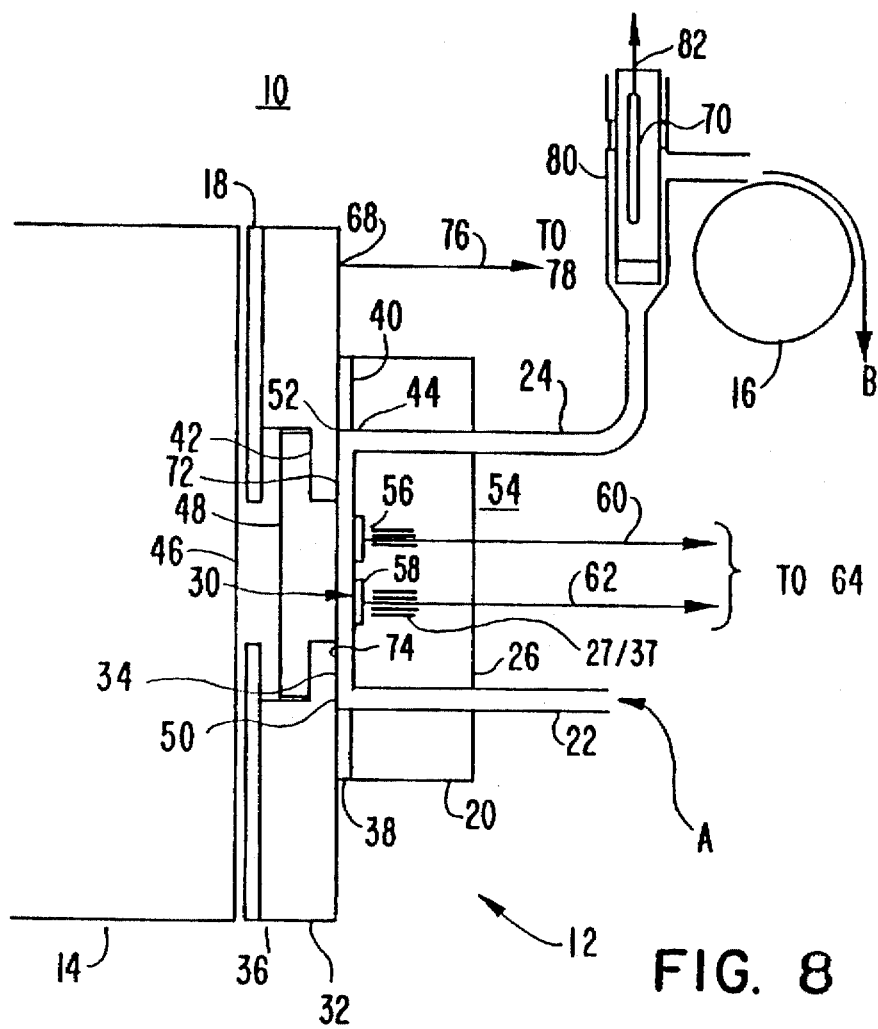
FIG. 8 is a schematic drawing of a cell for performing the microparticulate-based nonseparation and separation assays of the invention; the cell employs a working electrode and plurality of magnets as in FIGS. 1 and 2.

Apparatus for carrying out the assays of the invention is shown in FIGS. 1, 2, 3, 5, 7, 8 and 9. FIG. 8 discloses an advantageous ECL apparatus. The method may be employed in other types of ECL apparatus which include a working electrode or other triggering surface to provide electrochemical energy to trigger the ECL moiety into electrochemiluminescence, and the plurality of north-south magnets. While the methods of the invention can be carried out in a static or flow-through mode, apparatus 10 includes a flow-through cell, which provides distinct advantages for many types of samples including binding assay samples. Further details of apparatus for carrying out the ECL assays of the invention are disclosed in published PCT applications U.S. Ser. No. 89/04854 and U.S. Ser. No. 90/01370.

Apparatus 10 includes an electrochemical cell 12, a light detection/measurement device 14, which may advantageously be a photomultiplier tube (PMT), photodiode, charge coupled device, photographic film or emulsion or the like, and a pump 16, which is advantageously a peristaltic pump, to provide for fluid transport to, through and from cell 12. Alternatively, a positive displacement pump may be used. A shutter mechanism 18 is provided between cell 12 and PMT 14 and is controllably operated to open only so far as to expose PMT 14 to cell 12 during ECL measurement periods. The shutter mechanism may be closed, for example, during maintenance. Also included in apparatus 10 but not illustrated in FIG. 8 is a lightproof housing intended to mount the various components therein and to shield PMT 14 from any external light during the ECL measurements.

Cell 12 itself includes a first mounting block 20 through which passes an inlet tube 22 and an outlet tube 24, which may be advantageously constructed of stainless steel. Mounting block 20 has a first, outer surface 26 and a second, inner surface 28 defining one side of a sample-holding volume 30 of cell 12 in which cell 12 holds the cleaning and/or conditioning and/or measurement solutions during corresponding operations of apparatus 10. Inlet and outlet tubes 22, 24 pass through mounting block 20 from outer surface 26 to inner surface 28 and open into sample-holding volume 30. A second mounting block 32, advantageously constructed of stainless steel also has a first, outer surface 34 and a second, inner surface 36. Second mounting block 32 is separated from first mounting block 20 by an annular spacer 38, advantageously constructed of Teflon or other non-contaminable material. Thus, outer surface 34 of mounting block 32 defines part of the second side of the sample-holding volume 30. Spacer 38 has an outer portion 40 and a central aperture 42 whose inner edge 44 defines the side wall of sample-holding volume 30. Outer portion 40 seals the inner surface 28 of first mounting block 20 to outer surface 34 of second mounting block 32 to prevent any solution from passing out from sample-holding volume 30 between the two surfaces 28, 34. Mounting block 32 further has a central aperture 46 in which a window 48 is seal-fitted to define the rest of the second side of sample-holding volume 30 as a continuation of outer surface 34. Window 48 is formed of a material which is substantially transparent at the wavelength of electrochemiluminescent light emitted by the ECL moiety. Window 48 is therefore advantageously formed of glass, plastic, quartz or the like.

Inlet tube 22 intersects sample-holding volume 30 at a first end 50 thereof adjacent to spacer 38 and outlet tube 24 intersects sample-holding volume 30 at a second end 52 thereof, adjacent spacer 38. The combination of inlet tube 22, sample-holding volume 30 and outlet tube 24 thereby provides a continuous flow path for the narrow, substantially laminar flow of a solution to, through and from cell 12. Arrows A and B represent the flow into and out of inlet tube 22 and outlet tube 24, respectively.

Figure 2:
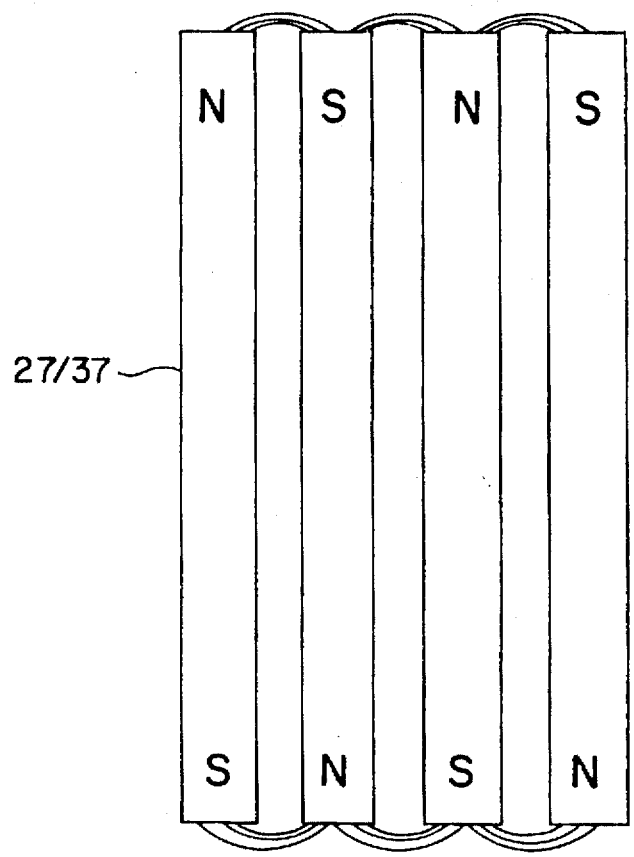

Mounted on inner surface 28 of first mounting block 20 is a working electrode system 54 which, in the illustrated embodiment, includes first and second working electrodes 56 and 58. In other embodiments, a single working electrode may advantageously be provided, or only electrode 56 may be a working electrode. Working electrodes 56, 58 are where the electrochemical and ECL reactions of interest can take place. Working electrodes 56, 58 are solid voltammetric electrodes and may therefore be advantageously constructed of platinum, gold, carbons or other materials which are effective for this purpose. Wire connectors 60, 62 connected to working electrodes 56, 58, respectively, pass out through first mounting block 20. Positioned vertically below the horizontally oriented electrode 56 or electrodes 56, 58 are a plurality of magnets 27/37 in north-south orientation as shown in FIGS. 1 and 2 and which are discussed in more detail below; see also FIGS. 3, 5 and 7 and discussion thereof below.

Figure 9:
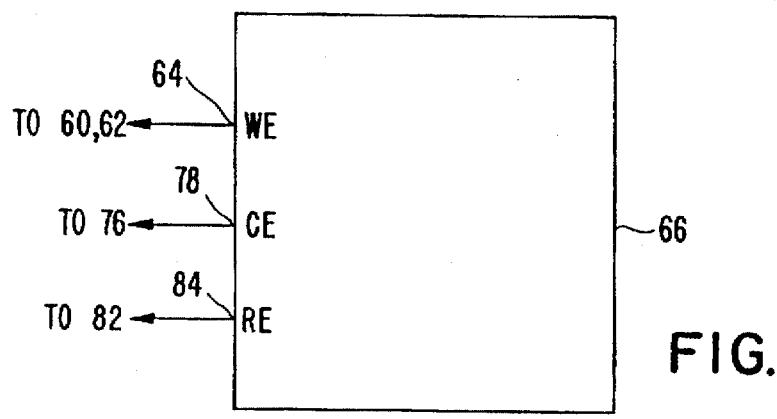
FIG. 9 is a simplified diagram of a voltage control apparatus for use with the cell of FIG. 8.

Connectors 60, 62 are both connected to a first, "working electrode" terminal 64 of a voltage control 66, illustrated in FIG. 9. Voltage control 66 advantageously operates in the manner of a potentiostat to supply voltage signals to working electrodes 56, 58 and optionally to measure current flowing therefrom during an ECL measurement. Alternatively, connectors 60, 62 may be connected to separate terminals of voltage control 66 for individual operation.

The potentiostat operation of voltage control 66 is further effected through a counter electrode 68 and, optionally but advantageously, a reference electrode 70. In the illustrated embodiment, mounting block 32 is made of stainless steel and counter electrode 68 consists in exposed surfaces 72, 74 of mounting block 32. Counter electrode 72, 74 and working electrodes 56, 58 provide the interface to impress the potential on the solution within sample-holding volume 30 which energizes the chemical reactions and triggers electrochemiluminescence in the sample and/or provides energy for cleaning and conditioning the surfaces of cell 12. Counter electrode 72, 74 is connected by a wire connector 76 to a second, "counter electrode" terminal 78 of voltage control 66.

Reference electrode 70 provides a reference voltage to which the voltage applied by the working electrodes 56, 58 is referred, for example, +1.2 volts versus the reference. Reference electrode 70 is advantageously located in outlet tube 24 at a position 80 spaced from cell 12 and is connected through a wire connector 82 to a third "reference electrode" terminal 84 of voltage control 66. In the three electrode mode, current may not flow through reference electrode 70. Reference electrode 70 may be used in a three electrode mode of operation to provide a poised, known and stable voltage and is therefore advantageously constructed of silver/silver chloride (Ag/AgCl) or is a saturated calomel electrode (SCE). Voltage control 66 may be operable in a two electrode mode of operation using only working electrode 56 and electrode 58 as a counter/reference electrode. In this two electrode mode of operation, counter/reference electrode 58 is electrically connected to voltage control terminals 78 and 84 on voltage control 66. In this case, voltage control 66 operates essentially as a battery. Voltage control 66 supplies voltage signals to working and counter electrodes 56 and 58 and optionally measures the current flowing through the respective electrodes. Reference electrode 70 may alternatively be a so-called "quasi-reference" electrode constructed of platinum, gold, stainless steel or other material, which provides a less stable voltage, yet one that is measurable with respect to the solution in contact. In both the two and three electrode mode, the reference electrode 70 or 58 serves the purpose of providing a reference against which the voltage applied to working electrodes 56 is measured. The poised voltage reference is currently considered to be more advantageous. Voltage control 66 in its potentiostat operation controls the various electrodes by providing a known voltage at working electrodes 56, 58 with respect to reference electrode 70 while measuring the current flow between working electrodes 56, 58 and counter electrode 72, 74. Potentiostats for this purpose are well known, and the internal structure of voltage control 66 may therefore correspond to any of the conventional, commercially available potentiostats which produce the above-recited functions and so do not form a part of the present invention per se. Indeed, apparatus 10 may alternatively be constructed without an internal voltage control 66, and may be adapted to be connected to an external potentiostat which is separately controlled for providing the required voltage signals to electrodes 56, 58, 72, 74 and 70. These voltage signals, applied in a specific manner as described below, provide repeatable initial conditions for the surfaces of working electrodes 56, 58 and advantageously for the surfaces of cell 12 as a whole, a feature which contributes significantly to improved precision in ECL measurements.

Pump 16 is advantageously positioned at outlet tube 24 to "pull" solution from a sample volume in the direction of arrow A into inlet tube 22. The solution will flow through inlet tube 22, sample-holding volume 30 and outlet tube 24 past reference electrode 70 and out in the direction of arrow B. Alternatively, pump 16 may be positioned at inlet tube 22 to "push" the solution through apparatus 10. Advantageously, this same flow path through inlet tube 22, sample-holding volume 30 and outlet tube 24 is used for all solutions and fluids which pass through cell 12, whereby each fluid performs a hydrodynamic cleaning action in forcing the previous fluid out of cell 12. Pump 16 may be controlled to suspend its operation to hold a particular solution in cell 12 for any period of time.

The flow-through construction of apparatus 10 permits working electrodes to be impressed with a variable voltage or to be continuously held at a preoperative potential while being continuously exposed to one or more solutions without exposing working electrodes 56, 58 (or counter and reference electrodes 72, 74, 70) to air. Exposure to air, which opens the circuit to the reference electrode 70, permits unknown, random voltage fluctuations which destroy the reproducibility of surface conditions on working electrodes 56, 58. The flow-through construction permits the rapid alternation between initializing steps, in which electrode system 54 is cleaned and conditioned, and measurement steps, in which one or more measurement waveforms or sweeps trigger ECL.

In the practice of the method and use of the apparatus of the invention, reagent compositions are used. The reagent compositions are the components of the assay systems of the invention, i.e., (a) electrolyte, (b) label compound containing an ECL moiety, (c) particles, including magnetically responsive particles, (d) analyte of interest or an analog of the analyte of interest, (e) a binding partner of the analyte of interest or of its analog, (f) a reactive component capable of reacting with (d) or (e), (g) a reductant, or (h) an electrochemiluminescence-reaction enhancer. The reagents may be combined with one another for convenience of use, i.e., two component, three component, and higher multiple component mixtures may be prepared, provided that the components are not reactive with one another during storage so as to impair their function in the intended assay. Desirably, the reagents are two-component or multicomponent mixtures which contain particles as well as one or more other components.

DESCRIPTION OF PREFERRED EMBODIMENTS OF THE INVENTION

While a wide range of particles can be employed in the particle-based assays of the invention, generally the particles are magnetically responsive or include magnetically responsive particles; and have a density of from 1.0 to 5.0 g/mL and preferably have a density of from 1.1 to 2 g/mL. Choice of the optimum density is within the skill of the art, the rate of settling in gravity-driven assays being a trade-off between the speed of the assay and the desire to create a uniform layer of complex on the electrode surface.

Particles having a wide range of mean diameters can also be employed. Particles having a mean diameter of from 0.001 to 200 µm such as 0.05 to 200 µm can be used; and preferably the particles have a mean diameter of from 0.01 to 10 µm.

Wide ranges of concentration of particles in the assay composition can also be employed. For example, the concentration can range from 1 to 10,000 µg/mL to preferably from 5 to 1000 µg/mL. Desirably, the density of the particles, their size and their concentration is selected such that the particles settle at a rate of at least 0.5 mm/min and preferably at a faster rate.

The art has described a number of magnetic particles which can be used in the assays of the invention. For example, U.S. Pat. Nos. 4,628,037, 4,695,392, 4,695,393, 4,698,302, 4,554,088, U.K. Patent Application GB 2,005, 019A and EP 0,180,384, all of which are hereby incorporated herein by reference, describe a variety of magnetic particles which can be used with success. The particles may be paramagnetic or ferromagnetic and may be coated with various materials to which binding compounds are coupled so that the magnetic particle can be used in immunoassays. Desirably the magnetic particles used in the invention have a susceptibility of at least 0.001 cgs units and desirably the susceptibility is at least 0.01 cgs units. The magnetic particles may have a broad range of densities, i.e. from substantially less than that of water, 0.01, to 5 g/mL and preferably from 0.5 to 2 g/mL. The particle sizes can range from 0.001 to 200, such as 0.001 to 100 or 0.05 to 200 µm and preferably from 0.01 to 10 µm. The concentration of the particles may range broadly from 1 to 10,000 µg per mL and preferably is from 5 to 1000 µg per mL.

Desirably the magnetic particles which are used have a low magnetic resonance, as described for example EP 0,180, 384, so that after the magnetic field is removed from the electrode surface, the particles demagnetize and can be swept out of the assay cell. Desirably the density, concentration and particle size of the magnetic particles is chosen such that the settling time is at least 0.5 mm/min and desirably it is above that rate. In operation of the magnetic cell it is often desirable to remove the magnet means from the electrode surface prior to inducing electrochemiluminescence in order not to interfere with the operation of the photomultiplier tube.

Assays

A variety of assays can be performed using the methods of the invention. These are described in more detail in the following Examples.

The following non-limiting Examples are given by the way of illustration and are not to be considered a limitation of this invention, many apparent variations of which are possible without departing from the spirit or scope thereof.

EXAMPLES

Instrumentation, Materials, and Methods (1) Instrumentation

A flow-through apparatus, as generally shown in FIGS. 1, 2, 3, 5, 7, 8 and 9, employing three electrodes, as described in FIGS. 8 and 9, and particularly having the plurality of north-south magnets described in FIGS. 1 and 2, is used.
Working Electrode—Au disk, 3 mm diameter
Counter Electrode—Au disk, 3 mm diameter
Reference Electrode—Ag/AgCl
Teflon Gasket (0.15" thick)
Plexiglas Faceplate
Inlet Tubing=0.042" id polypropylene
Aspiration Rates:variable from 0.01 to 5 mL/min
Potentiostat: microprocessor controlled
Luminometer using Hamamatsu R374 PMT (low gain red sensitive tube); PMT Voltage variable 0–1400 V
(2) Materials
(a) ECL Label Ru(bpy)$_3^{2+}$
(b) ECL Buffer 112 mM K$_2$PO$_4$, 88 mM K$_2$HPO$_4$·3H$_2$O, 50 µM NaCl, 6.5 mM NaN$_3$, 0.8 µM Triton X-100, 0.4 mM Tween 20, 100 mM tripropylamine in H$_2$O
(c) ECL Diluent 37.5 mM KH$_2$PO$_4$, 109.2 mM K$_2$HPO$_4$·3H$_2$O, 151.7 mM NaCl, 0.65 mM NaN$_3$, 0.43 mM bovine serum albumin in H$_2$O
(d) Ru(bpy)$_3^{2+}$-NHS R (2,2'-bipyridyl)$_2$(4-[3-(1,3-dioxolan-2-yl)propyl]-4'-methyl-2,2'-bipyridine)$^{2+}$
(e) Dynal Particles:
  (i) Dynal M-450 Dynabeads, 4.5 µm diameter superparamagnetic particles, 30 mg/mL, obtained from Dynal, 45 North Station Plaza, Great Neck, N.Y. 11021
  (ii) Dynal M-280 Dynabeads, 2.8 µM diameter superparamagnetic particles, 10 mg/mL, obtained for Dynal, 45 North Station Plaza, Great Neck, N.Y. 11021
(3) ECL Measurement Cycle (three electrode cell operation)
The ECL measurement cycle consists of three steps: (1) preconditioning, (2) measuring, and (3) cleaning. The preconditioning step involves the application of a voltage triangle wave of 0.0 V to +2.2 V to −1.0 V to +0.6 V at 2.0 V/sec. The measurement step involves the application of a triangle waveform from +0.6 V to +2.8 V to +2.0 V at 1.0 V/s. The cleaning step involves the application of a voltage square wave from +0.0 V to +3.0 V to −0.5 V to 0.0 V. All voltages are relative to the Ag/AgCl reference electrode.

Example 1

ECL Apparatus and Method for Deposition of Microparticles

Magnetic Collection using a Sedimentation Cell

Figure 3:
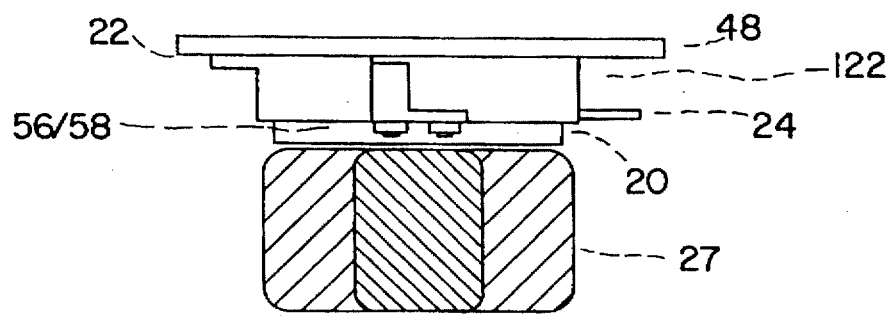
FIG. 3 is a schematic representation of a sedimentation assay cell which employs electromagnets of FIGS. 1 and 2 to cause the complex to settle on the electrode surface.

A cell such as a sedimentation cell for conduct of an assay using magnetic force generated by the plurality of north-south magnets of FIGS. 1 and 2 to cause the microparticulate to settle is shown in FIG. 3. Reference numeral 48 refers to a transparent window, reference numeral 122 to a gasket, reference numeral 22 to the inlet in the cell block, reference numeral 56, 58 to the working electrode, reference numeral 24 to the sample outlet, reference numeral 20 to the cell block itself and reference 27 to the plurality of electromagnets, as shown in FIGS. 1 and 2.

Figure 4:
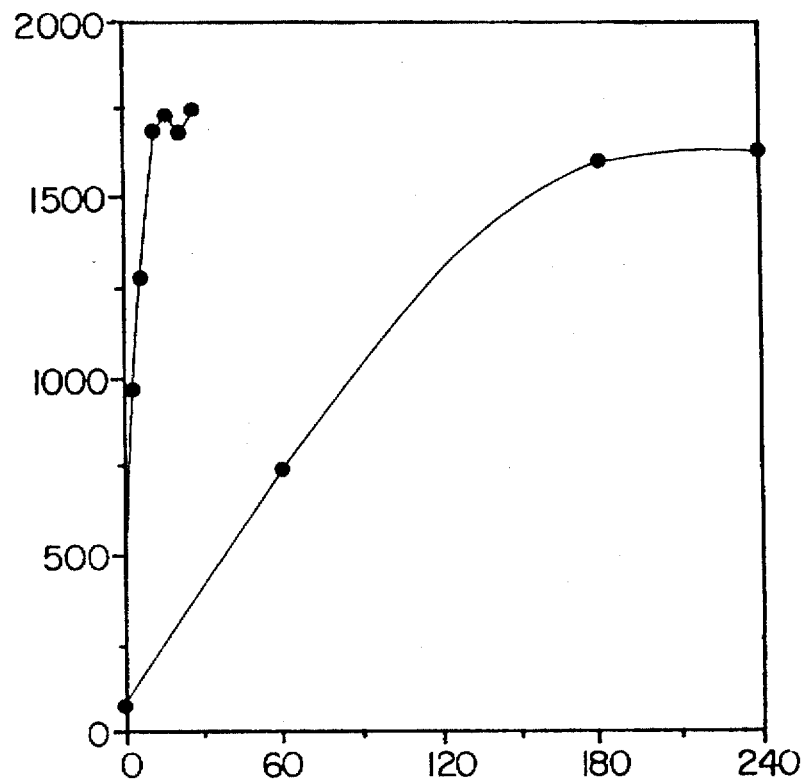
FIG. 4 is a graph showing the relative rates of settling of microparticulate complex under the influence of a magnetic field (FIGS. 1 and 2) and of gravity, respectively, i.e., a comparison of microparticulate settling times between a magnetic field (FIGS. 1, 2) induced settling and gravity settling wherein values for the magnetic field settling are represented by open circles and the values for gravity settling are represented by darkened circles.

The plane of the cell block is oriented horizontally; the plurality of magnets 27 is vertically below the magnets. Labeled microparticles (Dynal) in ECL buffer are drawn to the cell by means of a peristaltic pump. The pump is turned off after the microparticles reach the cell. The microparticles in the cell chamber are drawn to the working electrode by means of a magnetic field generated using a plurality of north-south electromagnets as shown in FIGS. 1 and 2 and shown generally in FIG. 3 as number 27, which for instance operate at 12 volts and 1.5 amps. By application of the electromagnets, the rate of deposition of microparticles is greatly increased over that observed when the microparticles settle solely due to the force of gravity. This is shown in FIG. 4.

Example 2

ECL Apparatus and Method for Deposition of Microparticles

Magnetic Collection using a Collection Cell

Figure 5:
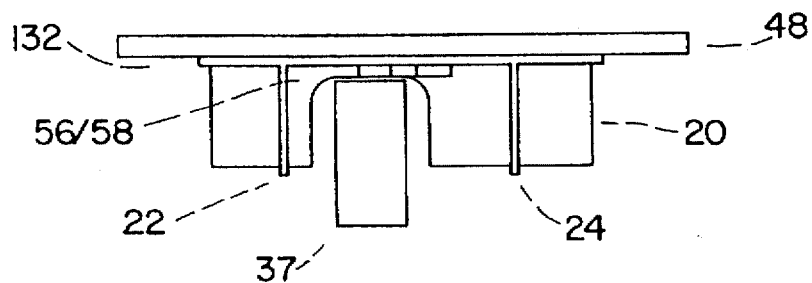
FIG. 5 is a schematic representation of a collection cell including a permanent magnets of FIGS. 1 and 2.

An assay is carried out in a cell such as a collection cell as described in FIG. 5. With reference to FIG. 5, reference numeral 48 refers to transparent window, reference numeral 132 to a gasket, reference numeral 22 to an inlet in the cell block, reference numeral 56, 58 to a working electrode, reference numeral 20 to the cell block itself, reference numeral 24 to the sample outlet and reference numeral 37 to a plurality of permanent magnets as shown in FIGS. 1 and 2.

The plane of the cell block is oriented horizontally; the plurality of magnets 37 is vertically below the magnets. Labeled microparticles (Dynal) in ECL buffer are drawn to the electrochemical cell by means of a peristaltic pump. Prior to the sample introduction, permanent magnets 37 are positioned immediately below the working electrode/solution interface at a distance of 0.035 inches. As the sample is being drawn to the cell, the microparticles deposit onto an area over the working electrode, as defined by the area of the magnets. The pump is turned off and the magnetic field withdrawn after the entire sample is deposited. The longer the collection time, the more particles are deposited. Increasing the concentration of particles on the working electrode results in an increased ECL intensity as shown in FIG. 6.

Example 3

Use of Magnet for Deposition of Microparticles

Magnetic Field Orientation

Microparticles 96 which are attracted to a plurality of magnets 27/37 as shown in FIGS. 1 and 2, whether they be permanent magnets or electromagnets, align with the orientation of the magnetic field 98, such as in FIG. 7 which depicts magnetic field 98 and the resultant particle arrangement 96 which is parallel to the surface of the working electrode 56/58, in the vicinity of that surface.

FIGS. 1 and 2 schematically show a cell and magnets 27/37 of FIGS. 3, 5, 7, 8 and 9 which is equipped with a magnet system which advantageously imposes field lines which are largely parallel to the plane of the electrode surface 56, 58. The magnet system consists of a plurality of individual permanent or electromagnets which are stacked and oriented such that the north and south poles of the magnets 27/37 alternate in the stack. The individual magnets of magnets 27/37 are separated by air or any non-magnetically responsive material. The arrangement as shown in FIGS. 1 and 2 advantageously applies magnetic lines of force to the region above the working electrode which are nearly horizontal to the plane of the electrode. This induces an orientation of the magnetically responsive particles in which the particles lie upon the surface of the electrode and are readily accessible to the electrochemical energy supplied by the electrode; see FIG. 7.

The magnet system 27/37 shown in FIGS. 1 and 2 also is advantageous in that the magnetic field lines do not extend a long distance from the magnet structure; see FIG. 7. The magnetic field from such a magnet system is not likely, therefore, to induce permanent magnetic behavior on ferromagnetic materials near the electrode apparatus and will not severely affect the operation of a photomultiplier tube near the flow cell apparatus.

Example 4

Coating of Particles With Labeled Non-specific Protein at Moderate Surface Concentration 30 mg (1 ml) of 4.5 μm uncoated magnetically responsive, polystyrene M-450 DYNABEADS (DYNAL, Oslo, Norway) were washed by magnetic separation with a 150 mM phosphate buffer pH 7.5 solution using 2 ml/wash. 150 μg of Ru(bpy)$_3^{2+}$-labeled mouse IgG (Jackson Immunochemicals) in 1 ml of phosphate buffer saline (PBS) with 0.05% thimerasol were added to the particles. This mixture was allowed to incubate overnight at room temperature with rotation. The solution was then magnetically separated from the particles and removed. To block unreacted sites, 1 ml of 3% BSA/PBS with 0.05% sodium azide was added to the particles, and the resultant solution was allowed to incubate 2 hours at room temperature. The particles were washed 5 times (2 ml/wash), and then finally resuspended in 6 ml of the same buffer for storage.

Example 5

Electrochemiluminescent (ECL) Measurement Using Magnetically Responsive Particles Uniform and nonuniform, polymeric and non-polymeric, magnetically responsive particles (Dynal, Oslo, Norway; Polysciences, Warrington, Pa. 18976; Cortex Biochem, San Leandro, Calif. 94577; Aldrich, Milwaukee, Wis. 53201) were coated with labeled proteins as described in Example 4. The coated particles were washed with ECL buffer three times before making 2 mL of a 300 μg/mL suspension. Using a peristaltic pump, 500 μl of the particle suspension is drawn into the flow cell (Example 2). As the particles flow to the working electrode, they are attracted and concentrated onto the working electrode surface by the magnets. Electrochemiluminescence using the magnetic particles is measured using a Hamamatsu R374 photomultiplier tube centered above the flow cell where particles concentrate on the working electrode surface. Table I shows representative ECL photoemission levels obtainable from the labeled-protein coated magnetically responsive particles.

TABLE I

| ECL Measurements from Different Magnetically Responsive Particles | | | | |
| --- | --- | --- | --- | --- |
| Particle Type | Diameter (μm) | Density (g/mL) | Material | ECL Counts |
| Glass | 8.0 | 2.4 | soda lime glass | 2200 |
|  | 2.0 | 2.4 | soda lime glass | 8500 |
| Quartz | 0.3–3.5 | 2.5 | SiO2 | 1150 |
| Gold | 1.0–2.0 | 19.3 | Au | 1100 |

Example 6

Preparation of Physically Adsorbed Sheep Anti-Thyroid Stimulating Hormone (TSH) Coated Dynal Particles (REAGENT I)

1 mL of 4.5 μm uncoated magnetic, polystyrene particles with —OH residues on their surface (DYNAL, DYNA-BEADS M-450, DYNAL A.S. Oslo, Norway) was washed by magnetic separation with a 150 mM sodium carbonate/bicarbonate pH 9.6 solution using 2 mL/wash. 0.5 mg of affinity purified Sheep anti-TSH, HCG scrubbed antibody (CIBA) in 1 mL of the carbo/bicarbo solution was added to the particles. This mixture was incubated overnight at room temperature with mixing. The solution was then magnetically separated from the particles and removed. 1 mL of 3% BSA/PBS w/0.05% sodium azide was added and incubated 2 hours at room temperature with agitation to block unreacted sites. The particles were washed 5 times (2 mL/wash) then finally resuspended in 1 mL of the same buffer for storage. The final concentration of Bead Reagent I was 3% by weight.

Example 7

Preparation of Ouabain-BSA Conjugate (REAGENT II)

ACTIVATION OF OUABAIN:

60.4 mg of ouabain octahydrate (Aldrich Cat# 14,193-3) in 6 mL of deionized (di) H$_2$O (wrapped in foil) was mixed with 87 mg of sodium metaperiodate (Mallinckrodt Cat# 1139) and the mixture was incubated at room temperature for 2 hours, rotating. The reaction was terminated by passing the reaction mixture through Dowex 1×8–50 ion exchange resin (Aldrich Cat# 21,740-9) with diH$_2$O. 200 μL 1M sodium phosphate pH 7.2 was added to adjust the pH of the solution to 7.0.

CONJUGATION OF ACTIVATED OUABAIN TO BSA:

50 mg of activated ouabain(4.6 mL) was then added dropwise to 108 mg bovine serum albumin BSA, Miles Fraction V) in 5 mL 0.15M PBS pH 7.8. This is a 40:1 (OUABIN:BSA) ratio. The reaction was incubated at room temperature for 2 hours, mixing, followed by rapid addition of 30 mg of sodium cyanoborohydride while mixing. Free ouabain and excess sodium cyanoborohydride were removed by dialysis at 4° C. in 0.15M PBS w/0.05% sodium azide pH 7.8. The Ouabain-BSA Conjugate Reagent II was stored at 4° C.

Example 8

Preparation of Physically Adsorbed Ouabain-BSA Coated Dynal Particles (REAGENT III)

5 mg of 4.5 μm uncoated magnetic, polystyrene particles with —OH residues on their surface (DYNAL, DYNA-BEADS M-450, DYNAL A. S. Oslo, Norway) were washed by magnetic separation with a 150 mM sodium carbonate/bicarbonate pH 9.6 solution using 10 mL/wash. 3 mg of Ouabain-BSA conjugate (Conjugate Reagent II) in 5 mL of the carb/bicarb solution was added to the particles. This mixture was incubated overnight at room temperature while rotating. The solution was then magnetically separated from the particles and removed. 5 mL of 3% BSA/PBS w/0.05% sodium azide was added and incubated 2 hours at room temperature, rotating to block unreacted sites. The particles were washed 5 times (10 mL/wash) then finally resuspended in 1 mL of the same buffer for storage. The final concentration of Bead Reagent III was 3% by weight.

Example 9

Preparation of Ru(bpy)$_3^{2+}$-Labeled Mouse Anti-Digoxin (REAGENT IV)

1 mg of mouse anti-Digoxin (Cambridge Medical Technologies Cat# 200-014 Lot A3575) was labeled with Ru(bpy)$_3^{2+}$. The monoclonal antibody (MAb) anti Digoxin antibody was buffer exchanged using Centricon 30 microconcentrators (Amicon) into 0.15M potassium phosphate buffer, 0.15M NaCl pH 7.8, the final volume being 0.5 mL. Immediately prior to use, 0.5 mg of Ru(bpy)$_3^{2+}$-NHS was dissolved with 125 μL of anhydrous dimethyl sulfoxide (Aldrich). To achieve a 25:1 molar ratio of Ru(bpy)$_3^{2+}$ to protein based on molecular weights of 1057 and 150,000 respectively, 0.18 mg Ru(bpy)$_3^{2+}$-NHS (45 μL) was added to the protein solution while shaking. The reaction tube was incubated in the dark at room temperature, 30 minutes, while shaking. The reaction was terminated by the addition of 25 μL of 1M glycine and incubated for 10 minutes. The reaction mixture was purified by passage through a Sephadex G—25 column (1×20 cm in 0.15M potassium phosphate, 0.15M NaCl with 0.05% sodium azide pH 7.2). The Ru(bpy)$_3^{2+}$-labeled mouse anti-digoxin fractions were collected and pooled. The labeled protein (Reagent IV) was determined to have 12 labels per protein molecule.

Example 10

Preparation of Ru(bpy)$_3^{2+}$-Labeled Mouse Anti-Thyroid Stimulating Hormone (TSH) (REAGENT V)

0.5 mg of mouse anti-TSH (CIBA) was labeled with Ru(bpy)$_3^{2+}$. The MAb anti TSH antibody was buffer exchanged using Centricon 30 microconcentrators (Amicon) into 0.15M potassium phosphate buffer, 0.15M NaCl pH 7.8, the final volume being 0.35 mL. Immediately prior to use, 0.5 mg of Ru(bpy)$_3^{2+}$-NHS was dissolved in 75 μL of anhydrous dimethyl sulfoxide (Aldrich). To achieve a 50:1 molar ratio of Ru(bpy)$_3^{2+}$ label to protein based on molecular weights of 1057 and 150,000 respectively, 0.176 mg Ru(bpy)$_3^{2+}$-NHS (26.4 μL) was added to the protein solution while shaking. The reaction tube was incubated in the dark at room temperature, 30 minutes, while shaking. The reaction was terminated by the addition of 25 μL of 1M glycine and incubated for 10 minutes. The reaction mixture was purified by passage through a Sephadex G—25 column (1×20 cm in 0.15M potassium phosphate, 0.15M NaCl with 0.05% sodium azide pH 7.2). The Ru(bpy)$_3^{2+}$-labeled mouse anti-TSH fractions were collected and pooled. The labeled protein (Reagent V) was determined to have 14 labels per protein.

Example 11

One Step Separation Sandwich Assay for Thyroid Stimulating Hormone (TSH)

100 μL serum calibrators (London Diagnostics TSH LumiTAG Kit), 25 μL Ru(bpy)$_3^{2+}$-labeled mouse anti-TSH (Reagent V) in ECL buffer and 25 μL Sheep anti-TSH-DYNAL particles (Reagent I) in ECL buffer were combined and incubated in polypropylene tubes for 15 minutes, at room temperature, with mixing. The particles were then washed by magnetic separation and then resuspending the particles in 500 μL of ECL buffer. This wash procedure was repeated two additional times. Finally, the particles were resuspended in 1 mL of ECL buffer. The electrochemiluminescence (ECL) for each sample is read as described in Example 2. The ECL counts are directly proportional to the concentration of analyte present in the sample (increasing counts as the concentration of analyte increases). Table II demonstrates a representative assay curve.

TABLE II

| One-Step Separation Sandwich Assay: Detection of TSH | | |
|---|---|---|
| TSH Concentration (μIU/mL) | ECL Counts (Duplicate Samples) | |
| 0.00 | 1918 | 1885 |
| 0.05 | 2584 | 2530 |
| 0.10 | 3365 | 3288 |
| 0.50 | 8733 | 8652 |
| 2.50 | 35688 | 35347 |
| 10.0 | 125316 | 136994 |
| 25.0 | 300248 | 288272 |
| 50.0 | 549034 | 564948 |

Example 12

One Step Non Separation Sandwich Assay for Thyroid Stimulating Hormone (TSH)

100 μL serum calibrators (London Diagnostics TSH LumiTAG Kit), 25 μL Ru(bpy)$_3^{2+}$-labeled mouse anti-TSH (Reagent V) in ECL buffer and 25 μL Sheep anti-TSH-DYNAL particles (Reagent I) in ECL buffer were combined and incubated in polypropylene tubes for 15 minutes, at room temperature, with mixing. Prior to reading results, 1 mL of ECL buffer was added. The electrochemiluminescence (ECL) for each sample is read as described in Example 2. The ECL counts are directly proportional to the concentration of analyte present in the sample (increasing counts as the concentration of analyte increases). Table III demonstrates a representative assay curve.

TABLE III

| One-Step Non-Separation Sandwich Assay: Detection of TSH | | |
|---|---|---|
| TSH Concentration (μIU/mL) | ECL Counts (Duplicate Samples) | |
| 0.00 | 2610 | 2769 |
| 0.05 | 2870 | 2894 |
| 0.10 | 2970 | 2950 |
| 0.50 | 3473 | 3403 |
| 2.50 | 5588 | 5495 |
| 10.0 | 13051 | 13139 |
| 25.0 | 26468 | 27306 |
| 50.0 | 47104 | 48664 |

Example 13

Two Step Separation Competitive Assay for Digoxin

50 μL serum calibrator (TDx Assay, Abbott Labs, Chicago, Ill. and 25 μL Ru(bpy)$_3^{2+}$-labeled mouse anti-digoxin (Reagent IV) in ECL buffer, were combined and incubated 20 minutes at room temperature with mixing. 25 μL Ouabain-BSA-DYNAL particles (Reagent III) in ECL buffer was added and incubated an additional 20 minutes, at room temperature, with mixing. The particles were then washed by magnetic separation and then resuspending the particles in 500 μL of ECL buffer. This wash procedure was repeated two additional times. Finally, the particles were resuspended in 1 mL of ECL buffer. The electrochemiluminescence (ECL) for each sample is read as described in Example 2. The ECL counts are inversely proportional to the concentration of analyte present in the sample (decreasing counts as the concentration of analyte increases). Table IV demonstrates a representative assay curve.

TABLE IV

Two-Step Separation Competitive Assay: Detection of Digoxin

| Digoxin Concentration (ng/mL) | ECL Counts (Duplicate Samples) | |
| --- | --- | --- |
| 0.0 | 22031 | 21154 |
| 0.5 | 13367 | 13638 |
| 1.0 | 9506 | 9607 |
| 2.0 | 5244 | 5129 |
| 3.0 | 2959 | 2994 |
| 5.0 | 1581 | 1631 |

Example 14

Two Step Non Separation Competitive Assay for Digoxin

50 µL serum calibrator (TDx Assay, Abbott Labs, Chicago, Ill.) and 25 µL Ru(bpy)$_3^{2+}$-labeled mouse anti-digoxin (Reagent IV) in ECL buffer, were combined and incubated 20 minutes at room temperature with mixing. 25 µL Ouabain-BSA-DYNAL particles (Reagent III) in ECL buffer was added and incubated an additional 20 minutes, at room temperature, with mixing. Prior to reading, the particles were resuspended in 1 mL of ECL buffer. The electrochemiluminescence (ECL) for each sample is read as described in Example 2. The ECL counts are inversely proportional to the concentration of analyte present in the sample (decreasing counts as the concentration of analyte increases). Table V demonstrates a representative assay curve.

TABLE V

Two-Step Non-Separation Competitive Assay: Detection of Digoxin

| Digoxin Concentration (ng/mL) | ECL Counts (Duplicate Samples) | |
| --- | --- | --- |
| 0.0 | 42051 | 39643 |
| 0.5 | 28721 | 28074 |
| 1.0 | 22190 | 21364 |
| 2.0 | 14660 | 14542 |
| 3.0 | 11315 | 11893 |
| 5.0 | 9161 | 8945 |

Example 15

Two Step Non Separation Competitive Assay for Digoxin Using a Read Cycle With Additional Washing of Final Reaction Sample on the Electrode 50 µL serum calibrator (TDx Assay, Abbott Labs, Chicago, Ill.) and 25 µL Ru(bpy)$_3^{2+}$-labeled mouse anti-digoxin (Reagent IV) in ECL buffer, were combined and incubated 20 minutes at room temperature with mixing. 25 µL Ouabain-BSA-DYNAL particles (Reagent III) in ECL buffer was added and incubated an additional 20 minutes, at room temperature, with mixing. Prior to reading, the particles were resuspended in 1 mL of ECL buffer. The electrochemiluminescence (ECL) for each sample is read as described in Example 2. The ECL counts are inversely proportional to the concentration of analyte present in the sample (decreasing counts as the concentration of analyte increases). Table VI demonstrates a representative assay curve.

Example 16

Preparation of Nucleic Acid Magnetic Particles And ECL Use

Dynal M 450 particles were activated with 2-fluoro-1-methylpyridinium toluene-4-sulfonate using standard procedures (6). These activated particles were then reacted with oligonucleotides JK8 and JK8C.

TABLE VI

Two-Step Separation Competitive Assay: Detection of Digoxin

| Digoxin Concentration (ng/mL) | ECL Counts (Duplicate Samples) | |
| --- | --- | --- |
| 0.0 | 42613 | 35309 |
| 0.5 | 24211 | 24168 |
| 1.0 | 17561 | 17206 |
| 2.0 | 10491 | 9909 |
| 3.0 | 6712 | 7145 |
| 5.0 | 4680 | 4603 |

To 100 mg of activated Dynal particles were added 33 nmoles of oligonucleotide in 650 µl of 0.1M NaHCO$_3$ followed by incubation for 3 hours with mixing. The particles were blocked by the addition of ethanolamine (4 mL, 0.1M). The coupled particles were mixed with 0.5 mg/mL single stranded salmon sperm DNA in ECL buffer, washed 4–5 times into ECL buffer and resuspended at 10 mg/mL in ECL buffer containing 100 µg/mL single stranded salmon sperm DNA.

The ability to detect ECL after hybridization to particles is demonstrated by the hybridization of particles coupled to JK8 and JK8C with Ru(bpy)$_3^{2+}$-label oligonucleotide JK7; JK7 is complementary to the JK8 sequence and not complementary to the JK8C sequence. Individual lots of particles (300 µg) in ECL buffer are mixed with 50 µl of ECL buffer containing 12.5, 6.3, 3.01 and 1.5 fmoles of label JK7. These mixtures are hybridized for 4 hours at 52° C. followed by washing with 1 mL ECL buffer and then resuspension on 830 µl of ECL buffer. The samples are analyzed as described in Example 2. At 12.5 fmoles the JK8 particles display over 1000 times more ECL counts than the JK8C particles; at 6.3 fmoles the JK8 particles display nearly 1000 times more ECL counts than the JK8C particles; and, at 3.02 and 1.5 fmoles, the JK8 particles display about 5 and about 3 times more ECL counts than the JK8C particles respectively. This demonstrates the ability to detect by specific hybridization the presence of specific sequences directly immobilized on the surface of particles by ECL.

Example 17

Preparation of Streptavidin Magnetic Particles I

Dynal M 450 particles were activated with 2-fluoro-1-methylpyridinium toluene-4-sulfonate using standard procedures (6). The activated particles were then reacted with streptavidin (Sigma Ltd). Activated particles (50 mg) were washed with 0.1M NaHCO$_3$ followed by the addition of streptavidin (1.5 mg) and reacted overnight. The particles were blocked by the addition of ethanolamine (4 mL, 0.1M). The coupled particles were mixed with 0.5 mg/mL single stranded salmon sperm DNA in ECL buffer, washed 4–5 times into ECL buffer and resuspended at 10 mg/mL in ECL buffer containing 100 µg/mL single stranded salmon sperm DNA. The streptavidin particles from Dynal M-280 also proved valuable but gives lower signals with the current assay sequence. For immunoassay applications particles were blocked with BSA after antigen or antibody coupling using the buffers used for passive coating.

Example 18

Preparation of Streptavidin Magnetic Particles II

To 15 mg of BSA (in 2–3 mL PBS), 105 µl of dimethylsulfoxide containing 50 mg/mL of biotin-x-NHS (Clontech, San Diego Calif. 5002-1) was added followed by mixing and incubation at room temperature for 30 minutes. The reaction was stopped by adding 30 µl of 1M glycine and incubation at room temperature for 10 minutes. The reaction mix was purified by gel filtration chromatography (Biorad, Bio-Gel P6). This biotin-BSA was filtered using 0.2 µm syringe. 5 mg biotin-BSA in 10 mL of 0.2M sodium carbonate/bicarbonate buffer pH 9.6 (carbonate/bicarbonate) buffer was added to 300 mg of Dynabeads washed with carbonate/bicarbonate (Dynal 14002). This mixture was Vortexed, and incubated overnight at room temperature with mixing. These particles were magnetically separated followed by the addition of 10 mL ECL diluent and 100 µl tRNA (10 mg/mL). This mixture was incubated for 3–4 hours at room temperature with mixing. These particles were washed once with 10 mL of ECL diluent and resuspended in 10 mL of ECL diluent and 100 µl tRNA (10 mg/mL). This mixture was mixed and incubated at 2°–6° C. overnight to stabilize proteins on particles. The particles were magnetically separated and suspended in 10 mL of PBS containing 15 mg of streptavidin (Scripps S1214) followed by mixing for one hour. The particles were washed 4 times in 10 mL ECL diluent, with 5 minutes mixing for each wash. The particles were finally resuspended in 29.7 mL of ECL diluent and 300 µl tRNA (10 mg/mL) to a final concentration of 10 mg/mL particles+100 µg/mL tRNA.

Example 19

Assay for Specific Genomic DNA Sequences

The assay format described here makes use of two oligonucleotides, both of which hybridize to the same DNA strand next to each other, one probe allows capture; the other labels the complex (sandwich hybridization). This assay was demonstrated using E. coli DNA and probes specific for the trp E/D gene region. The E. coli DNA was prepared following standard protocols (1). The salmon sperm control DNA was purchased from Sigma Ltd. To the samples of DNA were added 14 µl of hybridization buffer (10×PBS, 10 mM EDTA and 0.7% SDS), 2 ng of biotin labeled TRP.CO4 and 5 ng of Ru(bpy)$_3^{2+}$-label TRP.CO3. These samples were made up to 100 µl with water. The samples were heated to 97° C. and incubated at 97° C. for 10 min, cooled to 50° C. and hybridized for 2hrs. To these samples we added 20 µl of streptavidin coated magnetic particles II and mixed for 2hrs at room temperature. The particles were then washed 4 times in ECL buffer resuspended in 500 µl of ECL buffer and are analyzed as described in Example 2. The positive DNA is E. coli and the negative DNA is salmon sperm. The results obtainable are shown in Table VII.

TABLE VII

| DNA | Amount | Average ECL counts |
|---|---|---|
| Positive | 10 | 184 |
|  | 25 | 257 |
|  | 50 | 266.5 |
| Negative | 10 | 87 |
|  | 25 | 70 |
|  | 50 | 75 |

These results demonstrate the ability of the ECL assay system to function in the detection of a genomic gene in E. coli using a sandwich hybridization assay format on non amplified DNA. The streptavidin coated magnetic particles I can be similarly used in the fashion that the streptavidin coated magnetic particles II are used in this example.

Have thus described in detail preferred embodiments of the present invention, it is to be understood that the invention defined by the appended claims is not to be limited by particular details set forth in the above description as many apparent variations thereof are possible without departing from the spirit or scope of the present invention.

REFERENCES

1. Beaucage S. L., Caruthers M. H. Deoxynucleoside phosphoramidites, a new class of key intermediates for deoxypolynucleotide synthesis. Tetrahedron Lett 1982;22:1859–62.
2. Shibata D. K., Arnheim N., Martin J. W. Detection of human papilloma virus in paraffin-embedded tissue using the polymerase chain reaction. J Exp Med 1988;167:225–30.
3. Yanofsky, C. et al (1981) Nucleic Acids Res. 24, 6647–6668.
4. Updyke T. V., Nicolson G. L. Immunoaffinity isolation of membrane antigens with biotinylated monoclonal antibodies and streptavidin-agarose. Methods Enzymol 1986;121:717–25.
5. Cardullo R. A., Agrawal S., Flores C., Zamecnik D. C., Wolf D. E. Detection of nucleic acid hybridization by nonradiative fluorescence resonance energy transfer. Proc Natl Acad Sci 1988;85:8790–4.
6. Ngo T. T. Procedure for activating polymers with primary and or secondary hydroxyl groups. Makromol Chem Macromol Symp 1988;17:224–39.
7. Coutlee F., Bobo L., Mayur K., Yolken R. H., Viscidi R. P. Immunodetection of DNA with biotinylated RNA probes: A study of reactivity of a monoclonal antibody to DNA-RNA hybrids. Anal Biochem 1989;181:96–105.
8. Casadei J., Powell M. J., Kenten J. H. Expression and secretion of aequorin as a chimeric antibody using a mammalian expression vector. Proc Natl Acad Sci 1990;87:2047–51.
9. Molecular cloning, a laboratory manual 2nd Ed Sambrook, J. Cold Spring Harbor Laboratory New York
10. Heney, G. and Orr, G. A. (1981) Anal Biochem. 114, 92–96.
11. Mullis K. B., Faloona F. A. Specific synthesis of DNA in vitro via a polymerase-catalyzed chain reaction. Methods Enzymol 1987;155:335–50.
12. Lyons J., Janssen J. W. G., Bartram C., Layton M., Mufti G. J. Mutation of Ki-ras and N-ras oncogenes in myelodysplastic syndromes. Blood 1988;71:1707–12.
13. Saiki R. K., Gelfand D. H., Stoffel S., Scharf S. J., Higuchi R., Horn G. T., Mullis K. B., Erlich H. A. Primer-directed enzymatic amplification of DNA with a thermostable DNA polymerase. Science 1988;239:487–91.

14. Yee C., Krishnan-Hewlett I, Baker C. C., Schlegel R., Howley P. M. Presence and Expression of Human Papillomavirus sequences in human cervical carcinoma cell lines. Am J Pathol 1985;119:361–6.

15. Reddy E. P., Reynolds R. K., Santo E., Barbacid M. A point mutation is responsible for the acquisition of the transforming properties by the T24 humanbladder carcinoma oncogene. Nature 1982;300:149–52.

16. Marmur, J. (1961) J. Mol. Biol 3, 208.

What is claimed is:

1. A method for performing a binding assay for, and detecting or qauantitating, an analyte of interest in a sample comprising the steps of:

(a) forming a composition comprising:
      (i) said sample:
      (ii) an assay-performance-substance comprising an electrochemiluminescent label and containing at least one component selected from the group consisting of:
         (1) added analyte of interest or added analogue of said analyte;
         (2) a binding partner of said analyte or said analogue;
         (3) a reactive component capable of binding with component (1) or (2); and
      (iii) a plurality of magnetically responsive suspended particles to which are bound a binding partner of said analyte and/or said assay-performance-substance;

(b) incubating said composition to form a complex which includes a particle and said electrochemiluminescent label;

(c) introducing said composition into an assay cell;

(d) collecting said complex at the surface of an electrode by imposition of a magnetic field on said particles, said magnetic field being imposed by a plurality of magnets in north-south orientation;

(e) inducing the electrochemiluminescent label compound in said complex to electrochemiluminesce by imposing a voltage on said electrode; and (f) detecting or quantifying the electrochemiluminescence emitted at the electrode surface to detect or quantify the presence of the analyte of interest in the sample.

2. The method of claim 1 wherein the assay is a homogeneous assay.

3. The method of claim 1 wherein the assay is a heterogeneous assay.

4. The method of claim 3 further comprising a step of separating from the complex unbound components of the composition, wherein said seperating step is performed after the incubating step (b) and before the detecting or quantifying step (f).

5. The method of claim 4 wherein the separating step is before the inducing step (e).

6. The method of claim 4 wherein the separating step is prior to the introducing step (c).

7. The method of claim 5 wherein the separating step is performed after the collecting step (d), and comprises pumping a fluid into the assay cell, said fluid being substantially free of label or label reagents, thereby to wash from the complex any unbound components of the composition.

8. The method as defined in claim 1, wherein electrochemiluminescence emitted at said electrode surface is measured indirectly.

* * * * *